United States Patent

Milstein

[11] Patent Number: 5,976,569
[45] Date of Patent: *Nov. 2, 1999

[54] DIKETOPIPERAZINE-BASED DELIVERY SYSTEMS

[75] Inventor: Sam J. Milstein, Larchmont, N.Y.

[73] Assignee: Emisphere Technologies, Inc., Tarrytown, N.Y.

[*] Notice: This patent is subject to a terminal disclaimer.

[21] Appl. No.: 08/841,101

[22] Filed: Apr. 29, 1997

Related U.S. Application Data

[63] Continuation of application No. 08/315,200, Sep. 29, 1994, Pat. No. 5,693,338.

[51] Int. Cl.$^6$ .............. A61K 9/14; A61K 9/20; A61K 9/48; A61K 9/50
[52] U.S. Cl. .......... 424/451; 424/401; 424/405; 424/464; 424/465; 424/489; 514/2; 514/23; 514/54; 514/802; 514/805; 514/806; 514/807; 514/808; 514/889; 514/937; 514/951
[58] Field of Search ............... 424/451, 464, 424/489, 465, 405, 401; 514/2, 23, 54, 802, 805, 806, 807, 808, 889, 937, 951

[56] References Cited

U.S. PATENT DOCUMENTS

| | | | |
|---|---|---|---|
| Re. 24,899 | 11/1960 | Green . | |
| 2,671,451 | 3/1954 | Bolger | 128/260 |
| 2,828,206 | 3/1958 | Rosenberg | 99/2 |
| 2,862,918 | 12/1958 | Meyer et al. | 260/123.5 |
| 2,868,740 | 1/1959 | Luce | 260/8 |
| 2,971,916 | 2/1961 | Schleicher et al. | 252/62.5 |

(List continued on next page.)

FOREIGN PATENT DOCUMENTS

| | | | |
|---|---|---|---|
| 1077842 | 8/1976 | Canada | A61K 9/50 |
| 0 000 667 A1 | 2/1979 | European Pat. Off. | A61K 9/50 |
| 0 036 145 A1 | 9/1981 | European Pat. Off. | A61K 31/62 |
| 0 068 314 | 1/1983 | European Pat. Off. | A61K 31/16 |
| 0 105 804 | 4/1984 | European Pat. Off. | C12N 15/00 |
| 0 130 162 A2 | 1/1985 | European Pat. Off. | B01J 13/02 |

(List continued on next page.)

OTHER PUBLICATIONS

Airaudo, C.B. et al. (1987) *Journal of Food Science*, vol. 52(6), pp. 1750–1752.
Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S.W. et al. (1976) *BioSystems*, vol. 8, pp. 40–44.
Fox, S.W. et al., *Molecular Evolution and the Origin of Life*, Maxel Decker, New York (1977).
Fox, S.W. et al. (1968) *Biochim. Biophys. Acta*, vol. 160, pp. 246–249.
Fox, S.W. (1976) *Origins of Life*, vol. 7, pp. 49–68.
Fox, S.W. (1980) *Naturwissenschaften*, vol. 67, pp. 378–383.
Fox, S.W. et al. (1960) *Archives of Biochemistry and Biophysics*, vol. 86, pp. 281–285.
Fox, S.W. et al. (1974) *Origins of Life*, vol. 5, pp. 227–237.
Fox, S.W. (1984) *Origins of Life*, vol. 14, pp. 485–488.

(List continued on next page.)

*Primary Examiner*—Thurman K. Page
*Assistant Examiner*—James M. Spear
*Attorney, Agent, or Firm*—Darby & Darby

[57] ABSTRACT

Compositions useful in the delivery of active agents are provided. These delivery compositions include (a) an active agent; and either (b)(1) a carrier of (i) at least one amino acid and (ii) at least one diketopiperazine or (b)(2) at least one mono-N-substituted, di-N-substituted, or unsubstituted diketopiperazine. Methods for preparing these compositions and administering these compositions are also provided.

38 Claims, 6 Drawing Sheets

U.S. PATENT DOCUMENTS

| | | | |
|---|---|---|---|
| 3,016,308 | 1/1962 | Macaulay | 177/37 |
| 3,052,655 | 9/1962 | Fox et al. | 260/78 |
| 3,057,344 | 10/1962 | Abella et al. | 128/2 |
| 3,076,790 | 2/1963 | Fox et al. | 260/78 |
| 3,170,802 | 2/1965 | Fukushima et al. | 99/145 |
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato | 424/37 |
| 3,567,650 | 3/1971 | Bakan | 252/316 |
| 3,574,832 | 4/1971 | Engel et al. | 424/183 |
| 3,576,758 | 4/1971 | Emrick | 252/316 |
| 3,687,926 | 8/1972 | Arima et al. . | |
| 3,725,113 | 4/1973 | Chang | 117/82 |
| 3,748,277 | 7/1973 | Wagner | 252/316 |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum | 424/78 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,238,506 | 12/1980 | Stach et al. . | |
| 4,239,635 | 12/1980 | Rieder | 252/34 |
| 4,239,754 | 12/1980 | Sache et al. . | |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,393,192 | 7/1983 | Curatolo et al. | 528/292 |
| 4,402,856 | 9/1983 | Schnoring et al. | 428/402.22 |
| 4,402,968 | 9/1983 | Martin | 424/273 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,457,907 | 7/1984 | Porter . | |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,683,092 | 7/1987 | Tsang . | |
| 4,690,786 | 9/1987 | Ninomiya et al. | 264/4.6 |
| 4,692,284 | 9/1987 | Braden | 264/4.3 |
| 4,692,433 | 9/1987 | Hostetler et al. . | |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,878,942 | 11/1989 | Motegi et al. | 71/109 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,908,233 | 3/1990 | Takizawa et al. . | |
| 4,919,939 | 4/1990 | Baker | 424/493 |
| 4,925,673 | 5/1990 | Steiner | 424/455 |
| 4,927,928 | 5/1990 | Shroot et al. | 544/154 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. | 424/497 |
| 5,023,374 | 6/1991 | Simon | 564/152 |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. | 424/401 |
| 5,271,961 | 12/1993 | Mathiowitz et al. | 427/213.31 |
| 5,278,148 | 1/1994 | Branca et al. | 514/19 |
| 5,310,535 | 5/1994 | Kruper, Jr. et al. | 424/1.53 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,377 | 2/1995 | Chagnon et al. | 424/450 |
| 5,389,379 | 2/1995 | Dirix et al. | 424/451 |
| 5,401,516 | 3/1995 | Milstein et al. | 424/491 |
| 5,418,010 | 5/1995 | Janda et al. | 427/213.31 |
| 5,439,686 | 8/1995 | Desai et al. . | |
| 5,443,841 | 8/1995 | Milstein et al. | 424/451 |
| 5,447,728 | 9/1995 | Milstein et al. | 424/490 |
| 5,451,410 | 9/1995 | Milstein et al. | 424/490 |
| 5,474,997 | 12/1995 | Gray et al. . | |
| 5,536,813 | 7/1996 | Charpenel et al. . | |
| 5,540,939 | 7/1996 | Milstein et al. | 424/491 |
| 5,541,155 | 7/1996 | Leone-Bay et al. | 514/2 |
| 5,578,323 | 11/1996 | Milstein et al. | 424/499 |
| 5,601,846 | 2/1997 | Milstein et al. | 424/499 |
| 5,629,020 | 5/1997 | Leone-Bay et al. . | |
| 5,643,957 | 7/1997 | Leone-Bay et al. . | |
| 5,650,386 | 7/1997 | Leone-Bay et al. . | |
| 5,665,700 | 9/1997 | Cho et al. . | |
| 5,667,806 | 9/1997 | Kantor . | |

FOREIGN PATENT DOCUMENTS

| | | | |
|---|---|---|---|
| 0 170 540 A1 | 2/1986 | European Pat. Off. | A61K 9/52 |
| 0 342 054 A2 | 11/1989 | European Pat. Off. | A61K 7/06 |
| 0 342 056 A2 | 11/1989 | European Pat. Off. | A61K 7/06 |
| 0 365 183 | 4/1990 | European Pat. Off. | A61K 31/18 |
| 0 366 277 | 5/1990 | European Pat. Off. | A61K 9/107 |
| 0 418 642 | 3/1991 | European Pat. Off. | A61K 37/30 |
| 0 448 057 | 9/1991 | European Pat. Off. | C12P 21/08 |
| 0 452 161 | 10/1991 | European Pat. Off. | A61K 7/48 |
| 0 459 795 | 12/1991 | European Pat. Off. | A61K 37/02 |
| 0 467 389 | 1/1992 | European Pat. Off. | A61K 9/52 |
| 0 490 549 A1 | 6/1992 | European Pat. Off. | A61K 47/12 |
| 0 517 211 A1 | 9/1992 | European Pat. Off. | A61K 47/12 |
| 0 616 799 A1 | 9/1994 | European Pat. Off. | A61K 7/00 |
| 1 351 358 | 3/1964 | France . | |
| 1 468 601 | 2/1967 | France . | |
| 2 133 926 | 12/1972 | France | A61K 27/00 |
| 2 326 934 | 5/1977 | France | A61K 47/00 |
| 2 565 102 | 12/1985 | France | A61K 9/52 |
| 2 424 169 | 12/1974 | Germany | A61K 9/00 |
| 2343073 | 3/1975 | Germany . | |
| 3 202 255 | 10/1982 | Germany | C08L 89/00 |
| 3 612 102 | 10/1986 | Germany | C07K 15/00 |
| 71258/2 | 12/1987 | Israel . | |
| 48-24246 | 3/1973 | Japan . | |
| 56-68612 | 6/1981 | Japan | A61K 31/19 |
| 58-35111 | 3/1983 | Japan | A61K 9/66 |
| 6-107682 | 4/1994 | Japan . | |
| 280825 | 12/1964 | Netherlands . | |
| 280826 | 12/1964 | Netherlands . | |
| B-146698 | 11/1982 | Norway | A61K 37/26 |
| 929401 | 6/1963 | United Kingdom . | |
| 1 075 952 | 8/1967 | United Kingdom . | |
| 1 236 885 | 6/1971 | United Kingdom . | |
| 1 567 763 | 5/1980 | United Kingdom | A61K 9/22 |
| 2 095 994 | 10/1982 | United Kingdom | A61K 9/00 |
| 85/00110 | 1/1985 | WIPO | A61K 47/00 |
| WO 85/00105 | 1/1985 | WIPO | A61K 9/52 |
| 85/00809 | 2/1985 | WIPO . | |
| WO 87/04076 | 7/1987 | WIPO | A61K 45/02 |
| WO 88/01213 | 2/1988 | WIPO | B23B 5/16 |
| 92/19263 | 12/1992 | WIPO | A61K 39/00 |
| 93/18754 | 9/1993 | WIPO | A61K 9/16 |
| WO 93/25583 | 12/1993 | WIPO | C07K 15/00 |
| WO 94/11015 | 5/1994 | WIPO | A61K 37/00 |
| WO 94/14420 | 7/1994 | WIPO | A61K 9/16 |
| 94/18950 | 9/1994 | WIPO | A61K 9/127 |
| 94/18997 | 9/1994 | WIPO | A61K 37/00 |
| WO 94/21234 | 9/1994 | WIPO | A61K 7/00 |
| 94/24291 | 10/1994 | WIPO | A61K 39/015 |
| WO 94/23702 | 10/1994 | WIPO | A61K 9/16 |
| WO 94/23767 | 10/1994 | WIPO | A61L 9/16 |
| WO 94/28878 | 12/1994 | WIPO | A61K 9/14 |
| WO 95/11690 | 5/1995 | WIPO | A61K 37/00 |
| WO 85/02772 | 7/1995 | WIPO | A61K 49/00 |
| WO 95/28838 | 11/1995 | WIPO | A01N 37/46 |
| WO 95/28920 | 11/1995 | WIPO | A61K 31/19 |
| WO 96/12473 | 5/1996 | WIPO | A61K 9/16 |
| WO 96/12474 | 5/1996 | WIPO | A61K 9/16 |
| WO 96/12475 | 5/1996 | WIPO | A61K 9/16 |
| WO 96/21464 | 7/1996 | WIPO | A61K 39/00 |
| 96/30036 | 10/1996 | WIPO . | |
| WO 96/33699 | 10/1996 | WIPO | A61K 9/16 |
| WO 96/39835 | 12/1996 | WIPO | A01N 43/50 |
| WO 96/40070 | 12/1996 | WIPO | A61K 9/14 |
| WO 96/40076 | 12/1996 | WIPO | A61K 9/16 |
| 97/10197 | 3/1997 | WIPO . | |
| 97/31938 | 9/1997 | WIPO . | |
| 97/36480 | 10/1997 | WIPO . | |

OTHER PUBLICATIONS

Gol'dovskii, A.M. (1978) *Zhurnal Evolyutsionnoi Biokhimii i Fiziologii*, vol. 14(6), pp. 437–439.
Gurrieri, S. et al. (1973) *Thermochimica Acta*, vol. 7, pp. 231–239.
Harada, K. et al. (1979) *BioSystems*, vol. 11, pp. 47–53.
Harada et al., (1960) *Archives of Biochemistry and Biophysics*, vol. 86, pp. 274–280.
Hare (1970) *Etude Cenetique De La Polycondensation Thermique D'$_{X-Amino\ Acides}$*, vol. 45, pp. 330–339.
Heinrich, M.R. et al. (1969) *Archives of Biochemistry and Biophysics*, vol. 130, pp. 441–448.
Heinz, B. et al. (1981) *BioSystems*, vol. 14, pp. 33–40.
Hennon, G. et al. (1975) *Biochimie*, vol. 57, pp. 1395–1396.
Hsu, L.L. et al. (1976) *BioSystems*, vol. 8, pp. 89–101.
Hsu, L.L. et al. (1971) *Currents in Modern Biology*, vol. 4, pp. 12–25.
Ishima, Y. et al. (1981), *BioSystems*, vol. 14, pp. 243–251.
Jackson et al. (1991) "Pharmacological . . . ", *J. Pharm. & Exp. Thera.*, vol. 261, No. 1, pp. 546–552.
Jungck, J.R. et al. (1973) *Naturwissenschaften*, vol. 60, pp. 425–427.
Kokufuta, E. et al. (1984) *BioSystems*, vol. 16, pp. 175–181.
Krampitz, G. et al. (1967) *Naturwissenschaften*, pp. 516–517.
Krampitz, G. et al. (1968) *Naturwissenschaften*, pp. 345–346.
Krampitz, G. et al. (1966) *Naturwissenschaften*, pp. 7 and 8.
Lacey, Jr., J.C. et al. (1979) *BioSystems*, vol. 11, pp. 9–17.
Lacey, Jr., J.C. et al. (1979) *BioSystems*, vol. 11, pp. 1–7.
Martinez Luque–Romero, M. et al. (1986) *BioSystems*, vol. 19, pp. 267–272.
Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W.W. et al. (1976) *BioSystems*, vol. 8, pp. 45–50.
Melius, P. et al. (1987) *BioSystems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V.J.A. (1984) *Origins of Life*, vol. 14, pp. 513–522.
Olafsson, P.G. et al. (1971) *Polymer Letters*, vol. 9, pp. 521–528.
Phillips, R.D. et al. (1974) *Int. J. Peptide Protein Res.*, vol. 6, pp. 309–319.
Przybylski, A.T. et al. (1982) *Die Naturwissenschaften*, vol. 69, pp. 561–563.
Przybylski, A.T. et al. (1984) *Applied Biochemistry and Biotechnology*, vol. 10, pp. 301–307.
Przybylski, A.T. (1985) *BioSystems*, vol. 17, pp. 281–288.
Rohlfing, D.L. (1975) *Origins of Life*, vol. 6, pp. 203–209.
Rohlfing, D.L. (1970) *Science*, vol. 169, pp. 998–1000.
Rohlfing, D.L. (1967) *Archives of Biochemistry and Biophysics*, vol. 118, pp. 468–474.

Rohlfing, D.L. et al. *Catalytic Activities of Thermal Polyanhydro–α–Amino Acids*, pp. 373–418 (1970).
Rohling, D.L. et al. (1976) *BioSystems*, vol. 8, pp. 139–145.
Ryan, J.W. et al. (1973) *BioSystems*, vol. 5, pp. 115–118.
Saunders, M.A. et al. (1974) *BioSystems*, vol. 6, pp. 81–92.
Snyder, W.D. et al. (1975) *BioSystems*, vol. 7, pp. 222–229.
Sokol, P.E. (1974) *Journal of the American Oil Chemists'Society*, vol. 52, pp. 101–102.
Tschager et al. (1988) *Milchwirtschaftliche Berichte*, vol. 95, pp. 79–83.
Vaugha, G. et al. (1987) *BioSystems*, vol. 20, pp. 219–223.
Vol'kenshtein, M.V. (1989) *Molekulyarnaya Biologiya*, vol. 23(1), pp. 23–37.
Waehneldt, T.V. et al. (1968) *Biochim. Biophys. Acta*, vol. 160, pp. 239–245.
Williams et al. (1991) *J. Biol. Chem.*, vol. 266, No. 8, pp. 5182–5190.
Yuki, A. et al. (1969) *Biochemical and Biophysical Research Communications*, vol. 36(4), pp. 657–663.
Zulaski et al. (1983) "New Carboxyalkyl Inhibitors of Brain Enkenphalinase", *J. Med. Chem.*, 26, pp. 60–65.
(1985) *Chemical Abstracts*, vol. No. 105(1), Abstract No. 12027p.
(1985) *Chemical Abstracts*, vol. No. 102(6), Abstract No. 50870d.
*Chemical Abstract*, vol. 80(9) Abst. No. 52392a (1984).
Bergeron, Raymond J., et al. (1994) "Macromolecular Self–Assembly of Diketopiperazine Tetrapeptides", *Journal of the American Chemical Society*, vol. 116, pp. 8479–8484.
Bergeron, Raymond J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.
Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.
Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.
Bergeron, Raymond et al., "A Comparative Evaluation of Iron Clearance Models", *Annals New York Academy of Sciences*, pp. 278–393 (1991).
Andriuoli, G. et al. (1990), *Haemostasis* 20 (suppl. 1):154–158.
Caramazza, I., et al. (1991), *Thrombosis Research* 62:785–789.
Guarini, S., et al. (1983), *Experimentia* 41:350–352.
Guarini, S., et al. (1985), *Pharmacological Research Communications* 17 (8):685–697.
Dal Pozzo, A., et al. (1989), *Thrombosis Research* 56:119–124.
Gelb, R., et al (1983), *Lite Sciences* 33(1):83–85.
Watterberg et al. (1988), *Pediatric Research*, vol. 23, No. 4, part 2, p. 570A, column 1, abstract No. 2209.
Bernstein (1985), *Chest* 87(1):68S–73S.
Damge et al. (1988), *Diabetes* 37:246–251.
*Chemical Abstracts*:83 184360k, (1975).
Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".
Haas, S. et al., "Assessment Of Stability Of Proteinoid Microspheres", *Proceed. Intern. Symp. Control. Rel. Bioact. Mater.*, 20 (1993), Controlled Release Society, Inc.
X. Ma, et al., *Proceed. Intern. Symp. Control. Rel. Bioact. Mater.*, 20 (1993), Controlled Release Society, Inc. "In Vitro Mechanistic Investigation of the Proteinoid Microsphere Oral Delivery System".
Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.
Presented at "IBC Rational Drug Design Conference", San Diego, Calif.—Dec. 1994.
Leone–Bay et al., Presented at "Winter Conference on Medicinal and Bioorganic Chemistry" Steamboat Springs, Colorado—Feb. 1995 "Microsphere Formation and Drug Delivery in a Series of Derivatized Amino Acids".
Santiago et al., *Pharm. Res.* 11: 1194, p. S–298 "Oral Delivery of Heparin Microspheres made with Modified Amino Acids".
Leone–Bay et al., *Pharm. Res.* 11: 1994, p. S–121 "Oral Delivery of Heparin using Acylated Amino Acids".
Sarubbi et al., *Pharm. Res.* 11: 1994, p. S–299 "Oral Calcitonin Delivery using the PODDS Technology".
Leipold et al., *Pharm. Res.* 11: 1194, p. S–298 "Oral Delivery of Interferon in Rats and Primates".
Santiago et al., *Pharm. Res.* 11: 1994, p. S–298 "Evaluation in Rats of Vehicles for the Oral Delivery of Low Molecular Weight Heparin".
X. Ma et al., PDD 7303 *Pharmaceutical Research* 9(10):S–244, 1992 (Oct. Supplement).
Milstein et al., *Symposia Abstracts*. AAPS Annual Meeting, San Antonia, TX, Nov. 15–19, 1993.
Santiago et al. "Intitial Studies In The Assessment of Proteinoid Microsphere Activity" *Proceed. Intern. Symp. Control. Rel. Bioact. Mater.*, 20 (1993), Controlled Release Society, Inc.
Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., p. 116–117.
Santiago et al. "Proteinoid Microspheres For The Oral Delivery of Heparin" *Proceed. Intern. Symp. Control. Rel. Bioact. Mater.*, 19 (1992), Controlled Release Society, Inc. p. 514–515.
Santiago et al. *American Society for Microbiology* 92nd General Meeting, Abstract of the General Meeting, p. 159, May 26–30, 1992.
Milstein et al. "Preparation And In Vitro Characterization Of Proteinoid Microspheres" *Proceed Intern. Symp. Control. Rel. Bioact. Mater.*, 19 (1992), Controlled Release Society, Inc. p. 516–517.
Doris K. Chiappetta, *Eastern Analytical Symposium*, Nov. 17, 1992 "Solutions for Problems in Bioanalysis".
Elizabeth A. Harris. M.S., *Eastern Analytical Symposium*, Nov. 17, 1992 "Solutions for Problems in Bioanalysis".
*AAPS 6th Ann. Meeting and Expo.*, "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technolgy: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

Robert O. Dillman, M.D., *Annals of Internal Medicine*, 1989:111 pp. 592–600, "Monoclonal Antibodies for Treating Cancer".

Brendan D. Curti, *Critical Reviews in Oncology/Hematology*, 1993: 14 pp. 29–39 "Physical barriers to drug delivery in tumors".

V. Hird et al, *Genes and Cancer*, edited by Desmond Carney & Karol Sikora, pp. 183–189, Immunotherapy with Monoclonal Antibodies. (1991).

Michael E. Osband et al., *Immunology Today*, vol. 11, No. 6 1990, pp. 93–95, "Problems in the investigational study and clinical use of cancer immunotherapy".

William J. Harris, *Tibtech* Feb. 1993 vol. 11, pp. 42–44 "Therapeutic antibodies—the coming of age".

Thomas A. Waldmann, *Science*, Jun. 21, 1991, 252:1657–1662, "Monoclonal Antibodies in Diagnosis and Therapy".

*Chemical Abstracts*, 76(14):72994u, (1971).
*Chemical Abstracts*, 84(7):44660d, (1975).
*Chemical Abstracts*, 86(16):107529g, (1976).
*Chemical Abstracts*, 112(15):134663h, (1989).
*Chemical Abstracts*, 114(22):214519x, (1990).

J. Györe et al., *Thermal Analysis*, vol. 2—Proceeding Fourth ICTA Budapest 1974, p. 387–394.

*Chemical Abstracts*, 99(19) 158832b, (1982).

*Derwent Abstracts*, JP 67008622, (1967).

*Journal of Medicinal Chemistry*, vol. 38, No. 21, pp. 4257–4262, (1995), "Microsphere Formation in a Series of Derivatized α–Amino Acids: Properties, Molecular Modeling, and Oral Delivery of Salmon Calcitonin".

Andrea Leone–Bay et al., *Journal of Medicinal Chemistry*, vol. 38, No. 21, pp. 4263–4269, (1995), "N–Acylated α–Amino Acids as Novel Oral Delivery Agents for Proteins".

*The Extra Pharmacopoeia*, Thirtieth Edition, pp. 325–326, (1993).

Stephen J. Douglas et al., *Chemistry and Industry*, vol. 22:748–751, 1985.

C.A. Finch, *Chemistry and Industry*, vol. 22:752–756, 1985.

John A. Butera et al., *J. Med. Chem.*, vol. 34:3212–3228, 1990.

Madeline G. Cimini et al., *Ann. Report in Med Chem.*, vol. 27:89–98., 1992.

Bernadette Earley et al., *Brain Research*, vol. 546:282–286, 1991.

John W. Ellingboe et al., *J. Med Chem.*, vol. 35:705–716, 1992.

William C. Lumma et al., *J. Med Chem.*, vol. 30:758–763, 1987.

Joseph J. Lynch et al., *J. of Pharm. and Exp. Therap.*, vol. 269:541–554, 1994.

Kiyoshi Matsuno et al., *Brain Research*, vol. 575:315–319, 1992.

Thomas K. Morgan et al., *J. Med. Chem.*, vol. 33:1091–1097, 1990.

Hitoshi Oinuma et al., *J. Med Chem.*, vol. 33:903–905, 1990.

Tadimeti S. Rao et al., *Molecular Pharmacology*, vol. 37:978–982, 1990.

1.

N-Boc-γ-Benzyl-L-glutamic acid + Su-OH → N-Boc-Bz- OSu ester

2.

N-Boc-Bz- OSu ester → (pyridine, self-cyclization) → diketopiperizine dibenzyl ester (recrystal from E+OH)

3.

diketopiperizine dibenzyl ester → cis-diketopiperizine of L-glutamic acid

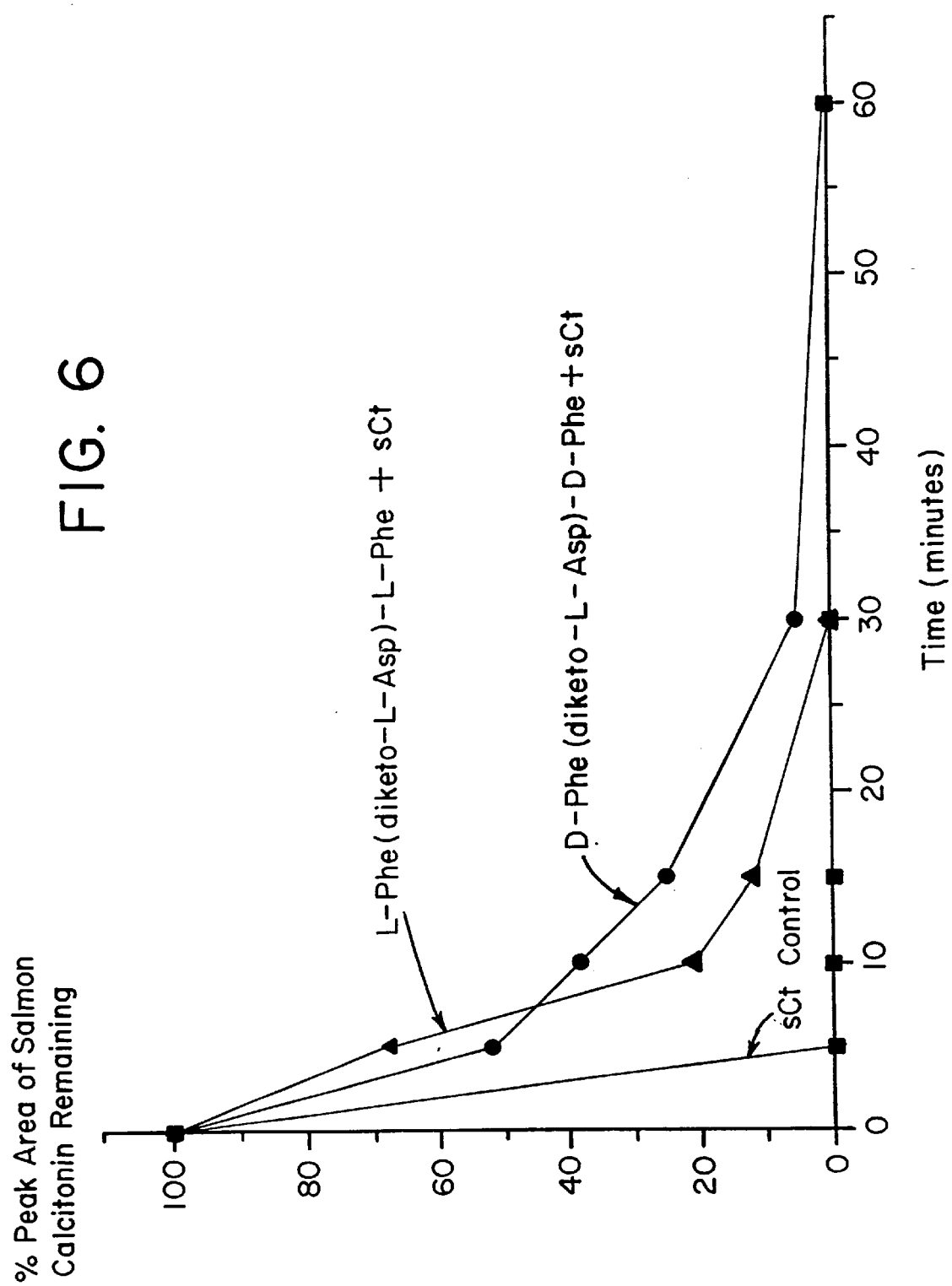

DIKETOPIPERAZINE-BASED DELIVERY SYSTEMS

This is a continuation, of application Ser. No. 08/315,200, filed Sep. 29, 1994. U.S. Pat. No. 5,693,338.

FIELD OF THE INVENTION

The present invention relates to compositions for delivering active agents, and particularly biologically active agents. The carriers in these compositions facilitate the delivery of a cargo to a target. These delivery compositions are particularly useful in the oral delivery of biologically active agents such as pharmacologically or therapeutically active agents. Methods for the preparation and for the administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself.

Biologically active agents are particularly vulnerable to such barriers. For example in the delivery to animals of pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically active agents would be the route of choice for administration to animals if not for biological, chemical, and physical, barriers such as varying pH in the gastrointestinal (GI) tract, powerful digestive enzymes, and active agent impermeable gastrointestinal membranes. Among the numerous agents which are not typically amenable to oral administration are biologically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastrointestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters*, Vol. 62, pg. 60; and Hashimoto etal. (1979), *Endocrinology Japan*, Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

Steiner et al., World Patent Publication No. WO93/18754, disclose a drug delivery system in which a drug cargo is encapsulated within a microparticle formed of specific di-substituted diketopiperazine sub-units. The diketopiperazines are only substituted with side chain substituents at two of the carbons in the ring, and at least one of those substituents must include an ionizable group. Neither the diketopiperazines nor the sub-units are combined with any other amino acid.

There is still a need in the art for simple, inexpensive delivery systems which are easily prepared and which can delivery a broad range of active agents.

SUMMARY OF THE INVENTION

Compositions useful in the delivery of active agents are provided. These delivery compositions comprise (a) an active agent; and (b) a carrier comprising (i) at least one amino acid or an ester or an amide thereof and (ii) at least one diketopiperazine. Preferably, the carrier comprises (i) at least two amino acids which are the same or different and (ii) at least one diketopiperazine. In an alternate embodiment, the delivery compositions comprise (a) an active agent, and (b) at least one mono-N-substituted, di-N-substituted, or unsubstituted diketopiperazine.

Biologically active agents and pharmacologically active agents may be incorporated as the active agent, and these compositions may be in the form of microspheres.

Also contemplated is a method for preparing these compositions wherein at least one active agent is mixed with a carrier as described above or wherein the carrier is solubilized in a solvent, and the carrier solution is contacted with the active agent and a precipitator solution in which the carrier is insoluble.

In a further embodiment, the compositions are administered, preferably orally, to animals.

BRIEF DESCRIPTION OF THE DRAWINGS

FIG. 6 is a graphic illustration of the results of an in vitro pancreatin Enzyme Kinetic study with calcitonin alone and with L-Phe-(diketo-L-Asp)-L-Pheand D-Phe-(diketo-L-Asp)-D-Phe carriers.

DETAILED DESCRIPTION OF THE INVENTION

Figure 1:
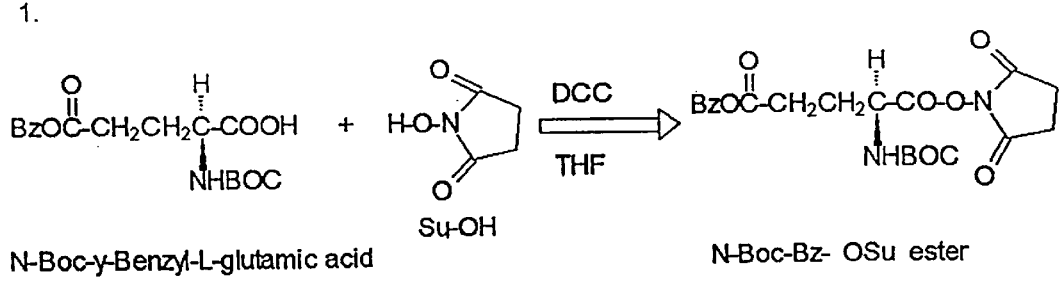
FIG. 1 is an illustration of a reaction scheme for the preparation of diketopiperazines.
Figure 1:
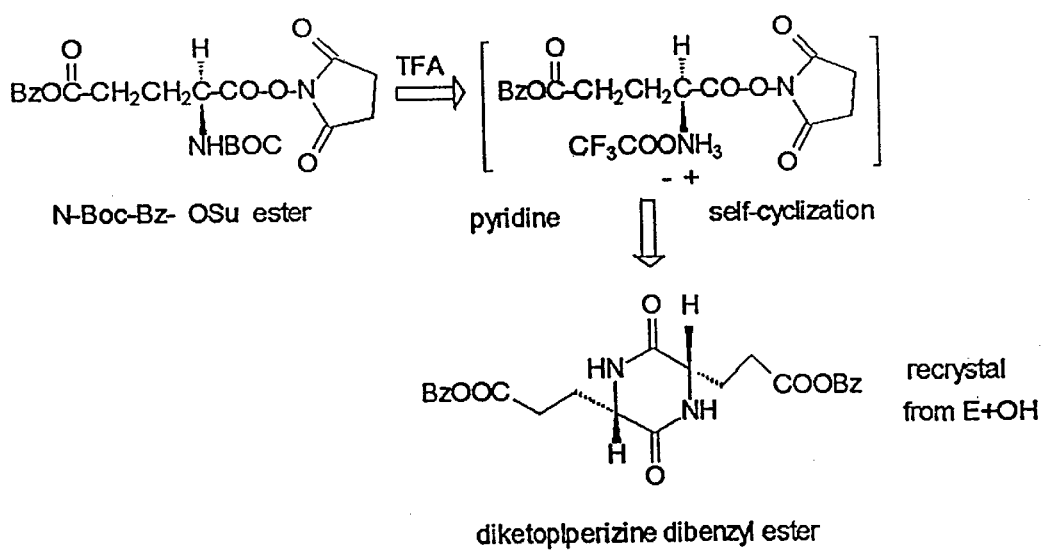
Figure 1:
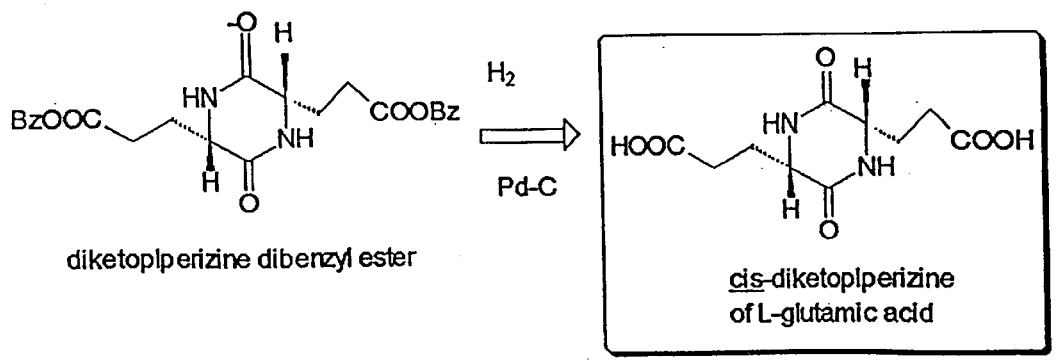

The present invention is suited to the delivery of any active agents through various biological, chemical, and physical barriers. It is particularly suited to the delivery of active agents which are subject to environmental degradation. Other advantages provided by the present invention include the use of readily available or easy to prepare, inexpensive starting materials. The formulation methods of the present invention are cost-effective for preparing and isolating these compositions, are simple to perform, and are amenable to industrial scale up for commercial production.

Active Agents

Active agents suitable for use in the present invention include biologically active agents, chemically active agents, including, but not limited to, fragrances, as well as other active agents such as, for example, cosmetics.

Biologically active agents include, but are not limited to, pesticides, pharmacological agents, and therapeutic agents. For example, biologically active agents suitable for use in the present invention include, but are not limited to, peptides, and particularly small peptides; hormones, and particularly hormones which by themselves do not or only pass slowly through the gastro-intestinal mucosa and/or are susceptible to chemical cleavage by acids and enzymes in the gastrointestinal tract; polysaccharides, and particularly mixtures of mucopolysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); antimicrobials, including, but not limited to anti-fungal agents; or any combination thereof.

The compositions of the present invention may include one or more active agents.

Carriers

Amino Acids

The amino acids which are combined with the diketopiperazines include any carboxylic acid having at least one free amine group and include naturally occurring and synthetic amino acids and all optional isomers thereof. The amino acids further include α- and non-α-amino acids.

Typical amino acids useful herein have the formula:

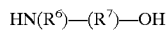
HN(R⁶)—(R⁷)—OH $R^6$ is hydrogen, $C_1$ to $C_{24}$ alkyl, $C_1$–$C_{24}$ alkenyl, phenyl, naphthyl, ($C_1$–$C_{10}$ alkyl) phenyl, ($C_1$–$C_{10}$ alkenyl) phenyl, ($C_1$–$C_{10}$ alkyl) naphthyl, ($C_1$–$C_{10}$ alkenyl) naphthyl, phenyl ($C_1$–$C_{10}$ alkyl), phenyl ($C_1$–$C_{10}$ alkenyl), naphthyl ($C_1$–$C_{10}$ alkyl), and naphthyl ($C_1$–$C_{10}$ alkenyl); optionally $R^6$ may be substituted with $C_1$–$C_4$ alkyl, $C_1$–$C_4$ alkenyl, $C_1$–$C_4$ alkoxy, —OH, —SH, —CO$_2$R⁸, or any combination thereof; $R^8$ is hydrogen $C_1$–$C_4$ alkyl, or $C_1$–$C_4$ alkenyl; and $R^6$ may optionally be interrupted by oxygen, nitrogen, sulfur, or any combination thereof.

The phenyl or naphthyl groups may optionally be substituted. Suitable, but non-limiting examples of substituents are $C_1$–$C_6$ alkoxy, —OH, —SH, or CO$_2$R¹⁰, wherein $R^{10}$ is hydrogen $C_1$–$C_6$ alkyl, or $C_1$–$C_6$ alkenyl.

$R^7$ has the formula

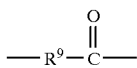

wherein $R^9$ is $C_1$ to $C_{24}$ alkyl, $C_1$ to $C_{24}$ alkenyl, phenyl, naphthyl, ($C_1$ to $C_{10}$ alkyl)-phenyl, ($C_1$ to $C_{10}$ alkenyl)phenyl, ($C_1$ to $C_{10}$ alkyl)naphthyl, ($C_1$ to $C_{10}$ alkenyl)naphthyl, phenyl ($C_1$ to $C_{10}$ alkyl), phenyl ($C_1$ to $C_{10}$ alkenyl), naphthyl ($C_1$–$C_{10}$ alkyl), and naphthyl ($C_1$–$C_{10}$ alkenyl); $R^9$ may optionally be substituted with $C_1$ to $C_{24}$ alkyl or $C_1$ to $C_{24}$ alkenyl; and $R^7$ may optionally be interrupted by oxygen, nitrogen, sulfur or any combination thereof.

The phenyl or naphthyl groups may optionally be substituted. Suitable but non-limiting examples of substituents are $C_1$ to $C_6$ alkyl, $C_1$ to $C_6$ alkenyl, $C_{1-C6}$ alkoxy, hydroxy, thio, or CO$_2$R¹¹ alkenyl, wherein $R^{111}$ is hydrogen, $C_1$–$C_6$ alkyl, or $C_1$–$C_6$ alkenyl.

The preferred naturally occurring amino acids for use as the amino acid component(s) of the carrier carriers of the present invention are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, or O-phosphoserine. The most preferred amino acids are arginine, leucine, lysine, phenylalanine, tyrosine, and valine.

The preferred non-naturally occurring amino acids for use herein β-alanine, phenylglycine, α-aminobutyric acid, γ-amino-butyric acid, 4-(4-aminophenyl)butyric acid, α-amino isobutyric acid, ε-aminocaproic acid, 7-aminoheptanoic acid, β-aspartic acid, aminobenzoic acid, aminohippuric acid, γ-glutamic acid, cysteine (ACM), ε-lysine, methionine sulfone, norleucine, norvaline, ornithine, d-ornithine, p-nitrophenylalanine, hydroxy proline, and thioproline.

The carriers of the present invention include at least one and preferably two amino acids. Any combination of amino acids may be used. Accordingly, two or more of the amino acids may be the same or different. The amino acids will be selected based upon the properties desired in the carrier such as, for example, solubility as described below.

Diketopiperazines

The diketopiperazines of the present invention are six member ring compounds. The ring includes two nitrogen atoms and is substituted at two carbons with two oxygen atoms. Preferably, the carbonyl groups are at the 1 and 4 ring positions. These rings can be optionally, and most often are, further substituted.

Preferred diketopiperazines are compounds of the formula:

II

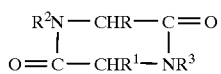

wherein R, $R^1$, $R^2$, and $R^3$ independently are hydrogen, $C_1$–$C_{24}$ alkyl, $C_1$–$C_{24}$ alkenyl, phenyl, naphthyl, ($C_1$–$C_{10}$ alkyl)phenyl, ($C_1$–$C_{10}$ alkenyl)phenyl, ($C_1$–$C_{10}$ alkyl) naphthyl, ($C_1$–$C_{10}$ alkenyl)naphthyl, phenyl ($C_1$–$C_{10}$ alkyl), phenyl ($C_1$–$C_{10}$ alkenyl), naphthyl ($C_1$–$C_{10}$ alkyl), and naphthyl ($C_1$–$C_{10}$ alkenyl); any of R, $R^1$, $R^2$, and $R^3$ independently may optionally be substituted with $C_1-C_4$ alkyl, $C_1-C_4$ alkenyl, $C_1-C_4$ alkoxy, —OH, —SH, and —$CO_2R^4$ or any combination thereof; $R^4$ is hydrogen, $C_1-C_4$ alkyl or $C_1-C_4$ alkenyl; and any of R, $R^1$, $R^2$, and $R^3$ independently may optionally be interrupted by oxygen, nitrogen, sulfur, or any combination thereof.

The phenyl or naphthyl groups may optionally be substituted. Suitable, but non-limiting, examples of substituents are $C_1-C_6$ alkyl, $C_1-C_6$ alkenyl, $C_1-C_6$ alkoxy, —OH, —SH, or $CO_2R^5$ wherein $R^5$ is hydrogen, $C_1-C_6$ alkyl, or $C_1-C_6$ alkenyl.

Preferably, when the diketopiperazine is polymerized with additional amino acids, R, $R^1$, or both R and $R^1$, contain at least one functional group, a functional group being a non-hydrocarbon portion responsible for characteristic reactions of the molecule. Simple functional groups are heteroatoms including, but not limited to halogens, oxygen, sulfur, nitrogen, and the like, attached to, the carbon of an alkyl group by a single or multiple bond. Other functional groups include, but are not limited to, for example, hydroxyl groups, carboxyl groups, amide groups, amine groups, substituted amine groups, and the like.

Similarly, $R^2$, $R^3$, or both $R^2$ and $R^3$ may contain a functional group as described above. Preferably, $R^2$ and $R^3$ independently are hydrogen, $C_1-C_4$ alkyl or $C_1-C_4$ alkenyl. If the diketopiperazine is to be used in an amino acids/diketopiperazine carrier, at least one R, $R^1$, $R^2$, and $R^3$ must include at least one functional group.

Special mention is made of diketopiperazines which are preferred carriers apart from being further combined with amino acid(s). These diketopiperazines include the unsubstituted diketopiperazines in which R, $R^1$, $R^2$, and $R^3$ are hydrogen, and diketopiperazines which are substituted at one or both of the nitrogen atoms in the ring, i.e. mono or di-N-substituted. Special mention is made of the N-substituted diketopiperazine wherein one or both of the nitrogen atoms is substituted with a methyl group.

Special mention is also made of diketopiperazines which are preferred components of the amino acids/diketopiperazine carriers of the present invention. Such preferred diketopiperazines are those which are substituted at one or two of the carbons of the ring and preferably are substituted with a functional group that includes at least one carboxyl functionality.

Diketopiperazinestypically are formed from α-amino acids. The "term" amino acid used with respect to diketopiperazines also includes any carboxylic acid having at least one free α-amine group and includes naturally occurring and synthetic α-amino acids and all optical isomers thereof. Preferably, the diketopiperazines are formed from two amino acids which are the same or optical isomers of one another. Typical amino acids useful in the preparation of diketopiperazines are the α-amino acids described above in the section "Amino Acids".

Preferably, the α-amino acids of which the diketopiperazines are derived are glutamic acid, aspartic acid, tyrosine, phenylalanine, and optical isomers of any of the foregoing. Most preferably, the diketopiperazines useful in the amino acids/diketopiperazine carriers of the present invention are prepared from trifunctional amino acids such as L-glutamic acid and L-aspartic acid which cyclize to form diketopiperazines.

Dipiperazine ring systems may be generated during thermal polymerization or condensation of amino acids or amino acid derivatives. (Gyore, J; Ecet M. *Proceedings Fourth ICTA (Thermal Analysis)*, 1974, 2, 387–394 (1974)). These six membered ring systems were presumably generated by intra-molecular cyclization of the dimer prior to further chain growth or directly from a linear peptide (Reddy, A. V., *Int. J. Peptide Protein Res.*, 40, 472–476 (1992); Mazurov, A. A. et al., *Int. J. Peptide Protein Res.*, 42, 14–19 (1993)).

Diketopiperazines can also be formed by cyclodimerization of amino acid ester derivatives as described by Katchalski et al., *J. Amer. Chem. Soc.*, 68, 879–880 (1946), by cyclization of dipeptide ester derivatives, or by thermal dehydration of amino acid derivatives and high boiling solvents as described by Kopple et al., *J. Org. Chem.*, 33 (2), 862–864 (1968).

A typical synthesis of a diketopiperazine is illustrated in FIG. 1. The COOH group(s) of an amino acid benzyl ester are activated in step 1 to yield a protected ester. The amine is deprotected and cyclized via dimerization in step, 2, providing a diketopiperazine di-ester. Finally in step 3, the COOH group(s) are deprotected to provide the diketopiperazine.

Amino Acids/Diketopiperazine Carriers

The preferred diketopiperazines generate a bis-carboxylic acid platform which can be further condensed with other amino acids to form the carriers of the present invention. Typically, the diketopiperazine will react and covalently bond with one or more of the amino acids through the functional group(s) of R, $R^1$, $R^2$, and/or $R^3$, and preferably R and/or $R^1$, of the diketopiperazines of Formula II above. These unique systems, because of the cis-geometry imparted by the chiral components of the diketopiperazine ring (Lannom, H. K. et al., *Int. J. Peptide Protein Res.*, 28, 67–78 (1986)), provide an opportunity systematically to alter the structure of the terminal amino acids while holding the orientation between them fixed relative to non-cyclic analogs (Fusaoka et al., *Int. J. Peptide Protein Res.*, 34, 104–110 (1989); Ogura, H. et al., *Chem. Pharma. Bull.*, 23, 2474–2477 (1975). See also, Lee, B. H. et al. *J. Org. Chem.*, 49, 2418–2423 (1984); Buyle, R., *Helv. Chim. Acta*, 49, 1425, 1429 (1966). Other methods of polymerization known to those skilled in the art may lend themselves to amino acid/diketopiperazine polymerization as well.

The amino acids/diketopiperazine carriers of the present invention may include one or more of the same or different amino acids as well as one or more of the same or different diketopiperazines as described above.

Ester and amide derivatives of these amino acids/diketopiperazine carriers are also useful in the present invention.

Delivery Systems

The carriers of the present invention are pharmacologically harmless, as are the microspheres prepared therefrom. They do not effectively impair the active (i.e. biological, chemical, therapeutical, pharmacological, or the like) agent.

The amino acid/diketopiperazine carriers of the present invention as well as the N-substituted or unsubstituted diketopiperazines described herein may be used to prepare compositions for delivering active agent cargoes, and particularly biologically active agent cargoes. Delivery compositions which include the active agent and the carrier may be in the form of mixtures of active agent and carrier or the carrier may form a microsphere which contains the active agent. The carrier described herein facilitates the delivery of the cargo to a target.

Microspheres containing an active agent can generally be of the matrix form or the microcapsule form. The matrix form includes both a hollow matrix sphere in which the carrier forms a matrix shell around a hollow center and the active agent is distributed throughout the matrix and a solid matrix sphere in which the carrier forms a spherical matrix continuum in which the active agent is distributed.

The microcapsule form is one in which the encapsulated active agent either is in solution or is a solid, with the carrier forming a shell around the encapsulated material. The microcapsule form is the form most often taken by the self assembly of the carriers of the present invention.

Delivery compositions may be mixtures which may be formulated simply by mixing the carrier with the active agent prior to administration. If the delivery composition is to be of the microsphere form, carrier microspheres can be prepared by dissolving the carrier in an appropriate solute and then stimulating self assembly by contacting the carrier solution with a precipitator. Solubility of the carrier can be regulated by the selection of the appropriate amino acids and/or diketopiperazine.

Furthermore, the diketopiperazines, the carriers, and therefore, the compositions of the present invention can be pH adapted to be selectively soluble in specific acidic, basic, or neutral pH ranges.

Delivery compositions which are targeted to an acidic environment can be made selectively soluble at acidic pH, such as the pH in the stomach. These compositions are prepared with an acid-soluble carrier. The acid-soluble carrier exists largely in the cation form in at least a portion of the pH range from about 1 to about 6.8. However, above about 6.8 or at selected ranges above pH 6.8, the carrier is largely unprotonated and insoluble in water. Therefore, the carrier could self assemble to microspheres at basic or neutral pH, and the active agent in the delivery composition would not be released until the carrier solubilizes upon encountering an acidic pH.

Delivery compositions which are to be targeted to an alkaline environment can be made selectively soluble at alkaline pH, such as the pH in the distal portion of the intestine. These compositions are prepared with a base-soluble carrier. The base-soluble carrier exists largely in an anionic form in at least a portion of the pH range of from about 7.2 to about 11. However, below and at pH 7.2, the carrier is largely protonated and insoluble in water. Therefore, the carrier could self assemble to microspheres at acidic or neutral pH, and the active agent in the delivery composition would not be released until the carrier solubilizes upon encountering a basic pH.

Delivery compositions which are targeted to a neutral environment can be made selectively soluble at neutral pH. These compositions are prepared with a neutral-soluble carrier. The neutral-soluble carrier exists largely in a neutral form at neutral pH, i,e. from about 6.8 to about 7.2. However, above or below this range, the carrier is insoluble in water. Therefore, the carrier could self assemble to microspheres at acidic or basic pH, and the active agent in the delivery composition would not be released until the carrier solubilizes upon encountering a neutral pH.

In a typical formulation, the final solution can contain from about 10 mg to about 2000 mg of carrier per ml of solution, preferably between about 75 to about 500 mg of carrier per ml of solution, and most preferably from about 75 to about 200 mg per ml. Optionally, the mixture is heated to a temperature between about 20° C. and about 60° C., preferably about 40° C., until the carrier dissolves. Particulates remaining in the solution may be filtered out by conventional means such as gravity filtration over filter paper. The carrier solution usually is maintained at the elevated temperature and is mixed with the active agent and a precipitator, for example, an acid solution such as, for example, aqueous acetic or citric acid at a concentration ranging from about 1N to about 3N for acid insoluble carriers, a basic solution for base insoluble carriers, and a neutralizing solution for neutral insoluble carriers. The active agent can be mixed with the precipitating solution or can be used separately. The resultant mixture is maintained for a period of time sufficient for microsphere formation as observed by light microscopy. Although it is preferred that the precipitating solution is added to the carrier solution, the carrier solution can be added to the precipitating solution as well.

The solutions above may optionally contain additives such as stabilizing additives. The presence of such additives promotes the stability and dispersability of the active agent in solution. The stabilizing additives may be employed at a concentration ranging between about 0.1 and 5% (w/v), preferably about 0.5% (w/v). Suitable, but non-limiting examples of stabilizing additives include buffer salts, gum acacia, gelatin, methyl cellulose, polyethylene glycol, and polylysine. The preferred stabilizing agents are gum acacia, gelatin, and methyl cellulose.

The amount of active agent which may be encapsulated by the microsphere is dependent upon a number of factors which include the concentration of agent in the encapsulating solution as well as the affinity of the agent for the carrier. The concentration of the active agent in the final formulation also will vary depending on the required dosage of treatment. When necessary, the exact concentration can be determined by, for example, reverse phase HPLC analysis.

When the present compositions are in microsphere form, the particle size of the microsphere can also aid in providing efficient delivery of the active agent to the target. Typically, microspheres of the present invention will have a diameter of less than 10 $\mu$m, preferably in the range of from about 0.1 $\mu$m to about 10 $\mu$m, and most preferably in the range of from 0.2 $\mu$m to about 10 $\mu$m. The size of the microspheres containing an active agent can be controlled by manipulating a variety of physical or chemical parameters, such as the pH, osmolarity, ionic strength of the encapsulating solution, or size of the ions in solution, and/or by the choice of the precipitator used in the microsphere forming and loading process.

For example, in the GI tract it is often desirable to use microspheres which are sufficiently small to deliver effectively the active agent at the targeted area within the gastrointestinal tract. Small microspheres can also be administered parenterally by suspending the spheres in an appropriate carrier fluid (e.g. isotonic solution) and injecting the solution directly into the circulatory system, intramuscularly, or subcutaneously. The mode of administration of the delivery compositions will vary, of course, depending upon the requirement of the active agent administered. It has been noted that large amino acid microspheres (greater than 50 $\mu$m) tend to be less effective as oral delivery systems.

The delivery compositions of the present invention may also include one or more enzyme inhibitors. Such enzyme inhibitors include, but are not limited to, compounds such as actinonin or epiactinonin and derivatives thereof. These compounds have the formulas below:

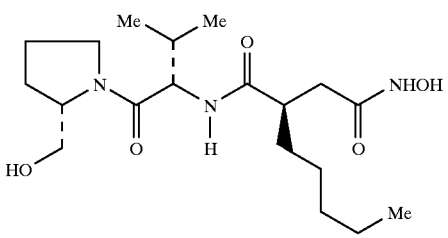

Actinonin

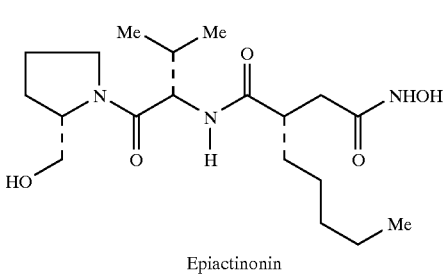

Epiactinonin

Actinonin derivatives have the formula:

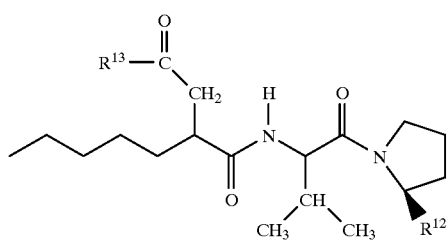

wherein $R^{12}$ is sulfoxymethyl or carboxyl or a substituted carboxy group selected from carboxamide, hydroxyaminocarbonyl and alkoxycarbonyl groups; and $R^{13}$ is hydroxyl, alkoxy, hydroxyamino or sulfoxyamino group. Other enzyme inhibitors include, but are not limited to, aprotinin (Trasylol) and Bowman-Birk inhibitor.

The delivery compositions of the present invention may be formulated into dosage units by the addition of one or more excipient(s), diluent(s), disintegrant(s), lubricant(s), plasticizer(s), colorant(s), or dosing vehicle(s). Preferred dosage unit forms are oral dosage unit forms. Most preferred dosage unit forms include, but not limited to, tablets, capsules, or liquids. The dosage unit forms can include biologically, pharmacologically, or therapeutically effective amounts of the active agent or can include less than such an amount if multiple dosage unit forms are to be used to administer a total dosage of the active agent. Dosage unit forms are prepared by methods conventional in the art.

The compositions of the subject invention are useful for administering biologically active agents to any animals such as birds; mammals, such as primates and particularly humans; and insects. The system is particularly advantageous for delivering chemical or biologically active agents which would otherwise be destroyed or rendered less effective by conditions encountered before the microsphere reaches its target zone (i.e. the area in which the active agent of the delivery composition are to be released) and within the body of the animal to which they are administered. Particularly, the compositions of the present invention are useful in orally administering active agents, especially those which are not ordinarily orally deliverable.

DESCRIPTION OF THE PREFERRED EMBODIMENTS

The following examples illustrate the invention without limitation.

Reagents were purchased from Sigma Chemical Co.—St. Louis, Mo., and were used without further purification. Flash column chromatography was performed on Silica gel 40 mm, obtained from J. T. Baker—Co. NMR spectra were recorded on Varian EM-390, VXR-300, or QE-300 instruments and were run with chemical shifts given in pats per million downfield from an internal tetramethylsilane or sodium 3-(trimethylsilyl)-propionate standard. Mass spectra were obtained on a Kratos MS 80 RFA or a Finnigan 4516 MS instrument. All optical rotations were performed at 589 nm (the Na D-line) at 22° C. on a Perkin-Elmer 241 polarimeter, with "c" expressed as g of compound per 100 ml of solvent. Melting points are uncorrected. Light microscopy was performed on a camera mounted-ZEISS light microscope. Scanning Electron Microscope (SEM) was performed on a Hitachi 4000 Scanning Electron Microscope and involved the generation of a white suspension by combining 100 μL of 0.45M citric acid and 50 μL of a 0.1M aqueous solution of the lithium salt of the peptide, described above. The aqueous suspension was deposited on polylysine-coated glass coverslips and fixed with 2% $OsO_4$ for 4 hours. The sample was washed with distilled water and air dried and sputtered with gold. SEM photographs were then obtained as described in the general section.

EXAMPLE 1

Diketopiperazine of L-glutamic Acid Dibenzyl Ester

NαBOC-γ-benzyl-L-glutamic acid (NBGA) (6.0 g, 17.8 mmol) and N-hydroxy succinimide (2.25 g, 19.6 mmol) were dissolved in anhydrous tetrahydrofuran (THF) (150 mL). The solution was cooled to 0° C. in an ice bath and dicyclohexylcarbodiimide (DCC) (4.04 g, 19.6 mmol) dissolved in 40 mL anhydrous THF was added dropwise over 30 minutes. The ice bath was removed.

The solution was allowed to warm to room temperature and was stirred overnight.

The reaction was monitored by thin layer chromatography (TLC) (20% $EtOH/CHCl_3$).

When the reaction was completed, the solution was filtered and the filtrate was concentrated to provide crude N-hydroxy succinimide (NHS) ester of NαBOC-γ-benzyl-L-glutamic acid as a viscous semi-solid (8.7 g).

Trifluoroacetic acid (TFA, 1.3 mL) was added dropwise to a portion of this NHS ester (0.50 g, 1.02 mmol) at 0° C. The solution was slowly allowed to warm to room temperature and was stirred overnight.

The volatile material was removed at reduced pressure, and a crude yellow solid (0.85 g) was recrystallized from EtOAc to provide pure diketopiperazine L-glutamic acid dibenzyl ester (0.11 g, 50%).

Properties of the diketopiperazine are listed below.

m.p. 275–277° C.; $^1$H NMR ($d_6$-DMSO): δ 8.26 (s,2H, NH), 7.46 (s, 10H, aromatic), 5.16 (s, 4H, $CH_2$), 3.98 (t, 2H, CH), 2.58 (m, 4H, CH2), 2.06 (m, 4H, CH2). Analysis: Calc. for $C_{24}H_{26}N_2O_6$: C 66.74, H 5.98, N 6.39: Found: C 65.73, H 6.03, N 6.35. Mass spectrum: Theoretical: 438.18; Found: 439 (M+1). Optical rotation: $[\alpha]_D$ –23.4° (c=1, dioxane).

EXAMPLE 2

Diketopiperazine of L-glutamic Acid

The diketopiperazine of L-glutamic acid dibenzyl ester was prepared according to the method of Example 1 (0.90 g, 2.05 mmol, 4.1 mequiv.) and was dissolved in a mixture of EtOAc/MeOH (6:1, 470 ml). Pd-C (0.20 g) catalyst was added. The black suspension was degassed three times, and hydrogen gas was introduced. The reaction was monitored by TLC (30% EtOH/CHCl$_3$).

The catalyst was filtered off, and the resultant diacid precipitate was washed five times with boiling MeOH and EtOAc to dissolve the diacid. The filtrate was concentrated to provide the diketopiperazine of L-glutamic acid as a white solid (0.53 g, 100%).

Properties of the diketopiperazine are listed below:

m.p. 234–236° C.; $^1$H NMR (d$_7$-DMF): δ 4.00 (t, 2H, CH), 2.49 (m, 4H, CH$_2$), 2.10 (m, 4H, CH$_2$). Analysis: Calc. for: C$_{10}$H$_{14}$N$_2$O$_6$: C 46.51; H 5.46; N 10.85: Found: C 46.72; H 5.50; N 10.82. High resolution mass spectrum: Theoretical: 259.0930 (M+H); Found: 259.033 (M+H). Optical rotation: [α]$_D$–52° (c=1, DMSO).

EXAMPLE 3

Diketopiperazine of L-aspartic Acid Dibenzyl Ester

The method of Example 1 was followed, substituting, β-benzyl-Nα-BOC-L-aspartic acid (24.0 g, 74.2 mmol) for the NBGA, 9.40 g (81.7 mmol) of the NHS, and 16.85 g (81.7 mmol) of the DDC in anhydrous THF to provide 37.13 g of crude NHS ester.

This NHS ester (37.13 g) was reacted with TFA (85 ml) at 0° C. to yield a crude TFA salt. The salt was neutralized in dry dimethylformamide (DMF) (100 mL) and pyridine (3.5 L) at 0° C. Recrystallization from EtOAc provided the diketopiperazine of L-aspartic acid dibenzyl ester as a white solid (7.13 g, 47%) m.p. 157° C.

Properties of the diketopiperazine are listed below.

1H NMR (CDCl$_3$) δ 7.31 (s, 10H, aromatic) 6.72 (s, 2H, NH), 5.12 (s, 4H, CH$_2$), 4.35 (m, 2H, CH), 3.00 (m, 4H, CH$_2$); Analysis: Calc. for C$_{22}$H$_{22}$N$_2$O$_6$: C 64.38; H 5.40; N 6.83: Found: C 64.27; H 5.39; N 6.79. High resolution mass spectrum: Theoretical: 410.1478: Found: 410.1503. Optical rotation: [α]$_D$–69.50' (c=1, CHCL$_3$).

EXAMPLE 4

Diketopiperazine of L-aspartic Acid

The diketopiperazine of L-aspartic acid dibenzyl ester (6.15 g, 15 mmol, 30 mequiv.) was prepared according to the method of Example 3 and was dissolved in MeOH (250 mL). Pd-C (0.90 g) catalyst was added. The black suspension was degassed three times, and hydrogen gas introduced. The reaction was monitored by TLC (30% EtOH/CHCl$_3$).

The catalyst was filtered off, and resultant diacid precipitate was washed five times with boiling MeOH to dissolve the diacid. The filtrate was concentrated to provide a white solid which was rinsed with MeOH and dried to provide the diketopiperazine of L.-aspartic acid as a white solid (2.78 g, 80%).

Properties of the diketopiperazine are listed below.

m.p. 254–255° C.; $^1$H NMR (CDCl$_3$-$_6$ DMSO, 1:1 by vol) δ 7.80 (s, 2H, NH), 4.20 (t, 2H, CH), 2.82 (D, 4H, CH$_2$). Analysis: Calc. for C$_8$H$_{10}$N$_2$O$_6$: C 41.75; H 4.38; N 12.17: Found: C 41.82; H 4.39; N 12.09. Optical rotation: [α]$_D$–37° (c=1, DMSO).

EXAMPLE 5

Bn-Gly-(diketo-L-Asp)-Gly-Bn

The cis-diketopiperazine of L-aspartic acid, prepared according to the method of Example 4, and glycine benzyl ester p-toluenesulfonate salt were dissolved in 10 ml of anhydrous DMF. Diphenylphosphorylazide (DPPA) (1.73 g, 6.3 mmol) was added dropwise at 0° C. over 5 minutes.

After stirring for 10 minutes, triethylamine (TEA) (1.38 g, 12.6 mmol) was added over 5 minutes. The reaction mixture was maintained under a nitrogen atmosphere, was stirred at 0° C. for an additional 30 minutes, and was allowed to warm to room temperature.

Removal of the volatile material under reduced pressure provided an oily residue which was dissolved in 30 ml methylene chloride and was washed in succession with 20 ml of H$_2$O, 1N HCl, saturated NaHCO$_3$, and an additional 20 ml of H$_2$O. The organic layer was separated, dried over anhydrous MgSO$_4$, filtered, and concentrated. Recrystallization of the crude product from CHCl$_3$/CH$_3$OH (1:1) provided Bn-Gly-(diketo-L-Asp)-Gly-Bn as tiny white crystals (73%).

Properties of the amino acids/diketopiperazine carrier are listed below.

m.p. 228–230° C.; $^1$H NMR (DMSO-d$_6$): δ 8.50 (m, 2H), 7.80 (s, 2H), 7.38 (m, 10H), 5.18 (s, 4H), 4.22 (m, 2H), 3.96 (m, 4H), 2.72 (m, 4H). $^{13}$C NMR (DMSO-d$_6$); δ 170.1, 169.8, 167.1, 135.8, 128.4, 128.0, 127.9, 65.9, 51.1, 40.7, 37.2. Analysis: Calc for C$_{26}$H$_{28}$N$_4$O$_8$: C 59.53; H 5.38; N 10.68: Found: C 59.43; H 5.37; N 10.69. Optical rotation: [α]$_D$–34° (c=1, DMSO).

EXAMPLE 6

Bn-L-Ala-(diketo-L-Asp)-L-Ala-Bn

The cis-diketopiperazine of L-aspartic acid, prepared according to the method of Example 4 (0.69 g, 3 mmol), and L-alanine benzyl ester hydrochloride (1.36 g, 6.3 mmol) were dissolved in 10 ml of anhydrous DMF solvent. Diphenylphosphorylazide (DPPA, 1.73 g, 6.3 mmol) was added dropwise at 0° C. over 5 minutes.

After stirring for 10 minutes, triethylamine (TEA) (1.38 g, 12.6 mmol) was added over 5 minutes. The reaction mixture was maintained under a nitrogen atmosphere, was stirred at 0° C. for an additional 30 minutes, and allowed to warm to room temperature overnight.

Removal of the volatile material under reduced pressure provided an oily residue which was dissolved in 30 ml of methylene chloride and was washed in succession with 20 ml of H$_2$O, 1N HCl, saturated NaHCO$_3$, and an additional 20 ml of H$_2$O. The organic layer was separated, dried over anhydrous MgSO$_4$, filtered, and concentrated to provide a pale yellow syrup which was recrystallized from CH$_3$OH to provide Bn-L-Ala-(diketo-L-Asp)-L-Ala-Bn as a white powder (0.9 g, 72%).

Properties of the amino acids/diketopiperazine carrier are listed below.

m.p. 218–219° C.; $^1$H NMR (DMSO-d$_6$); δ 8.50 (d, J=6.9 Hz, 2H), 7.81 (s, 2H), 7.36 (m, 10H), 5.12 (s, 4H) 4.42–4.35 (m, 2H), 4.19 (m, 2H), 2.63 (m, 4H), 1.30 (d, J=7.3 Hz, 6H); $^{13}$C NMR (DMSO-d$_6$): δ 172.4, 169.5, 167.0, 136.0, 128.4, 127.7, 65.8, 51.1, 47.7, 37.1, 16.9. Analysis: Calc. for C$_{28}$H$_{32}$N$_4$O8: C 60.86; H 5.84; N 10.14: Found: C 60.76; H 5.87; N 10.08. Optical rotation: [α]$_D$–67° (c=1, DMSO).

EXAMPLE 7

Bn-L-Val-(diketo-L-Asp)-L-Val-Bn

According to the method of Example 6, L-valine benzyl ester p-toluenesulfonate salt (0.80 g, 2.1 mmol) was condensed with the diketopiperazine of L-aspartic acid (0.23 g, 1 mmol) prepared according to the method of Example 4. The crude product was purified by flash chromatography on silica gel with EtOAc ($R_f$=0.2) to yield Bn-L-Val-(diketo-L-Asp)-L-Val-Bn (0.42 g, 69%).

Properties of the amino acids/diketopiperazine carrier are listed below.

m.p. 161–162° C.; $^1$H NMR CDCl$_3$): δ 7.42 (s, 2H), 7.33 (s, 10H), 7.10 (d, J=8.7, 2H), 5.21 (d, 2H), 5.10 (d, 2H), 4.61 (m, 2H), 4.30 (m, 2H), 3.44 (m, 4H), 2.14 (m, 2H) 0.85 (dd, 12H): $^{13}$C NMR (CDCl$_3$): 6 171.9, 170.1, 167.0, 135.1, 128.5, 128.4, 128.2, 67.1, 57.0, 51.7, 38.0, 31.1, 18.9, 17.5. Analysis: Calc. for $C_{32}H_{40}N_4O_8$: C 63.14; H 6.62; N 9.20: Found: C 63.13; H 6.65; N 9.11. Optical rotation: $[\alpha]_D$–75° (c=1, MeOH).

EXAMPLE 8

Bn-L-Tyr-(diketo-L-Asp)-L-Tyr-Bn

According to the method of Example 6, Bn-L-Tyr-(diketo-L-Asp)-L-Tyr-Bn was prepared by reacting the diketopiperazine of L-aspartic acid (0.46 g, 2 mmol) and L-Tyrosine benzyl ester p-toluenesulfonate salt (1.86 g, 4.2 mmol). The crude product was purified by flash chromatography on silica gel with CHCl$_3$/CH$_3$OH (10:1, $R_f$=0.4) to yield Bn-L-Tyr-(diketo-L-Asp)-L-Tyr-Bn (0.94 g, 65%).

Properties of the amino acids/diketopiperazine carrier are listed below.

m.p. 106–108° C.; $^1$H NMR (DMSO-d$_6$): δ 9.29 (s, 2H), 8.51 (d, J=7.3 Hz, 2H), 7.77 (s, 2H), 7.34 (m, 10H), 6.97 (d, J=8.4 Hz, 4H), 6.66 (d, J=8.4 Hz, 4H), 5.04 (s, 4H), 4.44 (m, 2H), 4.17 (m, 2H), 2.78 (m, 8H); $^{13}$C NMR (DMSO-d$_6$): δ 171.5, 169.8, 167.2, 156.1, 135.7, 130.1, 128.4, 128.0, 127.8, 126.8, 115.1, 65.9, 54.3, 51.1, 37.1, 36.2. Analysis: Calc. for $C_{40}H_{40}N_4O_{10}$: C 65.21; H 5.47; N 7.60: Found: C 64.82; H 5.41; N 7.49. Optical rotation: $[\alpha]_D$–41° (c=1, MeOH).

EXAMPLE 9

Bn-L-Phe-(diketo-L-Asp)-L-Phe-Bn

According to the method of Example 6, Bn-L-Phe (diketo-L-Asp)-L-Phe-Bn was prepared from the condensation of L-Phe benzyl ester p-toluenesulfonate salt (39.95 g, 93.4 mmol) and the diketopiperazine of L-Aspartic Acid prepared according to the method of Example 4 (10.0 g, 43.5 mmol). The crude product was precipitated from EtOAc. Flash chromatography (10% EtOH/CHCl$_3$) provided Bn-L-Phe-(diketo-LAsp)-L-Phe-Bn (23.2 g, 75%).

Properties of the amino acids/diketopiperazine carrier are listed below.

m.p. 148–149° C.; TLC (10% EtOH/CHCl$_3$, $R_f$=0.45).; $^1$H NMR (CDCl$_3$): δ 7.30 (m 18H), 7.01 (m, 4H), 6.87 (d, 2H), 5.12 (dd, 4H), 4.21 (d, 2H), 3.00 (m, 6H), 2.62 (dd, 2H). Analysis: Calc. for $C_{40}H_{40}N_4O_8$: C 68.17; H 5.72, N 7.95: Found: C 68.00; H 5.70; N 7.87. Optical rotation: $[\alpha]_D$–36° (c=0.25, CHCl$_3$).

EXAMPLE 10

Bn-D-Phe-(diketo-L-AsD)-D-Phe-Bn

N-t-Boc-D-Phe benzyl ester (14.2 g, 40 mmol) was dissolved in 50 ml of trifluoroacetic acid at 0° C. and was stirred for 30 minutes. Evaporation of the resulting mixture provided a yellow oil which was dissolved in 30 ml diethyl ether. The amine salt was precipitated, filtered, and dried (13.67 g, 93%, m.p. 110–111° C.).

According to the method of Example 6, the trifluoroacetate salt (13.2 g, 34 mmol) prepared above was condensed with the diketopiperazine of L-Aspartic Acid, (3.45 g, 15 mmol) prepared according to the method of Example 4. Removal of the volatile material under reduced pressure provided a yellow oil which was precipitated from MeOH (30 mL) and was chromatographed on silica gel (10% EtOH/CHCL$_3$, $R_f$=0.4) to yield Bn-D-Phe-(diketo-L-Asp)-D-Phe-Bn.

Properties of the amino acids/diketopiperazine carrier are listed below. (8.4 g, 80%), m.p. 172–173° C. $^1$H NMR (CDCl$_3$): δ 7.20 (m, 20H), 6.70 (d, J=8.1 Hz, 2H), 5.20 (d, 2H), 5.12 (d, 2H), 4.90 (m, 2H), 4.30 (m, 2H), 3.07 (m, 4H), 2.77 (m, 4H): $^{13}$C NMR (CDCl$_3$): δ 171.6, 169.3, 166.5, 135.5, 134.8, 129.1, 128.6, 127.1, 67.5, 53.2, 51.7, 38.6, 37.8. Analysis: Calc. for $C_{40}H_{40}N_4O_8$: C 68.17; H 5.72; N 7.95: Found: C 67.83; H 5.79; N 7.80. Optical rotation: $[\alpha]_D$–63° (c=0.94, 6% MeOH/CHCl$_3$).

EXAMPLE 11

Bn-D,L-Phe-(diketo-L-Asp)-D,L-Phe-Bn

According to the method of Example 6,D, L-phenylalanine benzyl ester hydrochloride salt (0.584 g, 2.1 mmol) was condensed with the diketopiperazine of L-Aspartic acid (0.23 g, 1 mmol) prepared according to the method of Example 4. The volatiles were removed under reduced pressure and the resultant yellow oil was chromatographed on silica gel (10% EtOH/CHCl$_3$, $R_f$=0.4) to yield Bn-D,L-Phe-(diketo-L-Asp)-D,L-Phe-Bn.

Properties of the amino acids/diketopiperazine carrier are listed below.

(0.4 g, 57%), m.p. 152–154° C.; $^1$H NMR (d$_6$-DMSO); δ 8.56 (d, J=7.9 Hz, 2H), 7.77 (d, J=9.4 Hz, 2H), 7.24 (m, 20H), 5.05 (m, 4H), 4.58 (m, 2H), 4.19 (m, 2H), 3.00 (m, 8H): $^{13}$C NMR (CDCl$_3$); δ 171.3, 169.7, 167.0, 136.8, 135.6, 129.1, 128.3, 128.0, 127.9, 127.8, 126.6, 65.9, 53.7, 51.0, 38.6, 37.0. Analysis: Calc. for $C_{40}H_{40}N_4O8$: C 68.17; H 5.72; N 7.95: Found: C 68.17; H 5.71; N 7.95. Optical rotation: $[\alpha]_D$–66° (c=0.33, DMSO).

EXAMPLE 12

Bn-L-Phe-(diketo-L-Glu)-L-Phe-Bn

According to the method of Example 6, Bn-L-Phe-(diketo-L-Glu)-L-Phe-Bn was prepared from the condensation of L-Phe benzyl ester p-toluenesulfonate salt (1.90 g, 4.46 mmol) and the diketopiperazine of L-Glu, (0.50 g, 1.94 mmol) prepared according to the method of Example 2. The crude product was recrystallized from EtOAc to provide Bn-L-Phe-(diketo-L-Glu)-L-Phe-Bn.

Properties of the amino acids/diketopiperazine carrier are listed below.

(1.10 g, 77%), m.p. 118–119° C.; $^1$H NMR (d$_6$-DMSO): δ 8.40 (d, 2H), 8.10 (s, 2H), 7.30 (m, 20H), 5.08 (m, 4H), 4.50 (m, 2H), 3.70 (t, 2H) 2.95 (m, 4H), 2.18 (m, 4H), 1.79 (m,4H). High resolution mass spectrum ($C_{42}H_{44}N_4O_8$): Theoretical: (M+H) 733.3237: Found: (M+H) 733.3246. Optical rotation: $[\alpha]_D$–25° (c=0.5, DMSO).

EXAMPLE 13

Bn-L-Phe-L-Phe-(diketo-L-Asp)-L-Phe-L-Phe-Bn

N-t-Boc-L-Phe-L-Phe benzyl ester (1.20 g, 2.4 mmol) was dissolved in 10 ml of trifluoroacetic acid at 0° C. and was stirred for 3 minutes. Evaporation of the volatile material at reduced pressure provided a white solid (1.35 g). The white solid was combined with the diketopiperazine of L-Asp prepared according to the method of Example 4 (0.25 g, 1.1 mmol, 2.2 mequiv) and was dissolved in dry DMF. The solution was cooled to 0° C., and DPPA (0.66 g, 2.4 mmol) followed by TEA (1.08 g, 10.6 mmol) were added. The solution was warmed to room temperature, and was stirred overnight. Removal of the volatile material under reduced pressure provided a white solid which was boiled in EtOAc and was filtered to provide Bn-L-Phe-L-Phe-(diketo-L-Asp)-L-Phe-L-Phe-Bn(0.95 g, 87%), m.p 223–224° C.

Properties of the amino acids/diketopiperazine carrier are listed below.

$^1$H NMR (d$_6$-DMSO); δ 8.45 (d, 2H) 8.15 (d, 2H), 7.15 (m, 30H), 5.00 (s, 4H), 4.47 (m, 4H), 4.10 (t, 2H), 3.00 (m, 8H), 2.65 (m, 4H). Analysis: Calc. for $C_{58}H_{58}N_6O_{10}$: C 69.72; H 5.85; N 8.41: Found: C 69.83, H 5.90; N 8.36. Optical rotation: $[\alpha]_D$-35.5° (c=0.51, DMSO).

EXAMPLE 14

Gly-(diketo-L-Asp)-Gly

A black suspension of Bn-Gly-(diketo-L-Asp)-Gly-Bn (0.71 g, 1.35 mmol) prepared according to the method of Example 5 and Pd-C (0.08 g, 10%) catalyst in 20 ml THF was degassed and was flushed with nitrogen three times. The reaction vessel was evacuated, and hydrogen gas was introduced. The hydrogenation was monitored by TLC (10% MeOH/CHCl$_3$, R$_f$=0.33). The catalyst was filtered off and washed with hot DMF. The crude product was purified by column chromatography (Sephadex LH-20, 15% EtOH/toluene) and recrystallized from methanol to yield Gly-(diketo-L-Asp)-Gly (0.41 g, 89%).

Properties of the amino acids/diketopiperazine carrier are listed below.

m.p. 240–242°; $^1$H NMR (d$_6$-DMSO); δ 8.37 (m, 2H), 7.78 (s, 2H), 4.21 (m, 2H), 3.78 (m, 4H), 2.62 (m, 4H). $^{13}$C NMR (DMSO-d$_6$): δ 171.4, 170.2, 167.1, 51.3, 40.7, 37.5. Analysis: Calc. for $C_{12}H_{16}N_4O_8$: C 41.86; H 4.69; N 16.27: Found: C 42.18, H 4.84; N 15.93, Mass spectrum; Theoretical: 344; Found: 345 (M+1). Optical rotation: $[\alpha]_D$-44° (c=1, DMSO).

EXAMPLE 15

L-Ala-(diketo-L-Asp)-L-Ala

A black suspension of Bn-Ala-(diketo-L-Asp)-L-Ala-Bn (0.83 g, 1.35 mmol), prepared according to the method of Example 6, and Pd-C (0.08 g, 10%) catalyst in 20 ml THF was degassed and was flushed with nitrogen three times. The reaction vessel was evacuated, and hydrogen gas was introduced. The hydrogenation was monitored by TLC (10% MeOH/CHCl$_3$, R$_f$=0.33). The catalyst was filtered off and was washed with hot DMF. Concentration of the filtrate and recrystallization of the crude solid from CH$_3$OH to yield L-Ala-diketo-L-Asp)-L-Ala (0.5 g, 90%).

Properties of the amino acids/diketopiperazine carrier are listed below.

m.p. 234–235° C.; $^1$H NMR (DMSO-d6): δ 12.55 (br, 2H), 8.31 (d, J=7.3 Hz, 2H), 7.78 (s, 2H), 4.20 (m, 4H), 2.66 (m, 4H), 1.26 (d, J=7.3 Hz, 6H). $^{13}$C NMR (DMSO-d$_6$): δ 174.2, 169.4, 167.0, 51.2, 47.5, 37.4, 17.3. Analysis: Calc. for $C_{14}H_{20}N_4O_8$: C 45.16; H 5.41; N 15.15: Found: C 45.09; H 5.45, N 14.94. Optical rotation: $[\alpha]_D$-65° (c=1, DMSO).

EXAMPLE 16

L-Val-(diketo-L-Asp)-L-Val

According to the method of Example 15, L-Val-(diketo-L-Asp)-L-Val was prepared by hydrogenation of its dibenzyl ester Bn-L-Val-(diketo Asp)-L-Val-Bn (0.4 g, 0.66 mmol) prepared according to the method of Example 7 using the procedure described in Example 1 5, except that the solvent used was MeOH (degassed). The resultant crude solid was purified by column chromatography (Sephadex LH-20, 15% EtOH/toluene) to provide L-Val-(diketo-L-Asp)-L-Val as a white solid (0.25 g, 89%), m.p. 217–218° C.

Properties of the amino acids/diketopiperazine carrier are listed below.

$^1$H NMR (CD$_3$OD); δ 4.33 (m, 4H), 4.17 (s, 2H), 2.94 (m, 4H), 2.17 (m, 2H), 0.97 (dd, 12H). $^{13}$C NMR (CD$_3$OD); δ 174.9, 172.2, 169.3, 59.1, 53.1, 39.2, 31.6, 19.6, 18.4. Analysis: Calc. for $C_{18}H_{28}N_4O_8 \cdot H_2O$: C 50.46; H 6.59; N 13.08: Found: C 50.49; H 6.65; N 12.87. Optical rotation: $[\alpha]_D$-54° (c=1, MeOH).

EXAMPLE 17

L-Tyr-(diketo-L-Asp)-L-Tyr

According to the method of Example 16, L-Tyr-(diketo-L-Asp)-L-Tyr was prepared by hydrogenation of the dibenzyl ester Bn-L-Tyr-(diketo-L-Asp)-L-Tyr-Bn (0.65 g, 0.88 mmol) prepared according to the method of Example 8. The reaction was monitored by TLC (11% EtOH/CHCl$_3$). Filtration of the catalyst and removal of the volatile material provided L-Tyr-(diketo-L-Asp)-Lr-Tyr (0.48 g, 98%).

Properties of the amino acids/diketopiperazine carrier are listed below.

m.p. 154–156° C.; $^1$H NMR (DMSO-d$_6$): δ 9.30 (br. s, 2H), 8.27 (d, J=6.7 Hz, 2H), 7.72 (s, 2H), 7.01 (d, J=7.1 Hz, 4H), 4.35 (m, 2H), 4.17 (S, 2H), 2.70 (m, 8H). $^{13}$C NMR (DMSO-d$_6$): 171.1, 169.7, 167.2, 156.0, 130.1, 127.5, 115.1, 54.1, 51.2, 37.4, 36.2. Analysis: Calc. for $C_{26}H_{28}N_4O_{10} \cdot H_2O$: C 54.35; H 5.26; N 9.75: Found: C 54.42; H 5.20; N 9.63. Optical rotation: $[\alpha]_D$-3.4° (c=1, MeOH).

EXAMPLE 18

L-Phe-(diketo-L-Aso)-L-Phe

According to the procedure of Example 16, L-Phe-(diketo-L-Asp)-L-Phe was prepared by hydrogenation of the dibenzyl ester (23.2 g, 32.9 mmol) Bn-L-Phe-(diketo-L-Asp)-L-Phe-Bn prepared according to the method of Example 9. The reaction was monitored by TLC (10% EtOH/CHCl$_3$). The resultant crude solid was recrystallized in EtOAc to provide L-Phe-(diketo-L-Asp)-L-Phe as a white solid (15.83 g, 92%).

Properties of the amino acids/diketopiperazine carrier are listed below.

m.p. 156–158° C.; $^1$H NMR (CD$_3$OD) δ 7.25 (m, 10H), 4.65 (dt, 2H), 4.28 (t, 2H), 3.19 (dd, 2h), 2.98 (dd, 2H), 2.81

(m, 4H). $^{13}$C NMR (CD$_3$OD) δ 174.7, 171.8, 169.1, 138.3, 130.3, 129.5, 127.8, 55.19, 53.0, 39.3, 38.4. Analysis: Calc. for C$_{26}$H$_{28}$N$_4$O$_8$: C 59.54; H 5.38; N 10.68: Found: C 59.60; H 5.49; N 10.53. High resolution mass spectrum: Theoretical: 525.1985 (M+H): Found: 525.2190 (M+H). Optical rotation: [α]$_D$–13° (c=0.75, MeOH).

Figure 2:
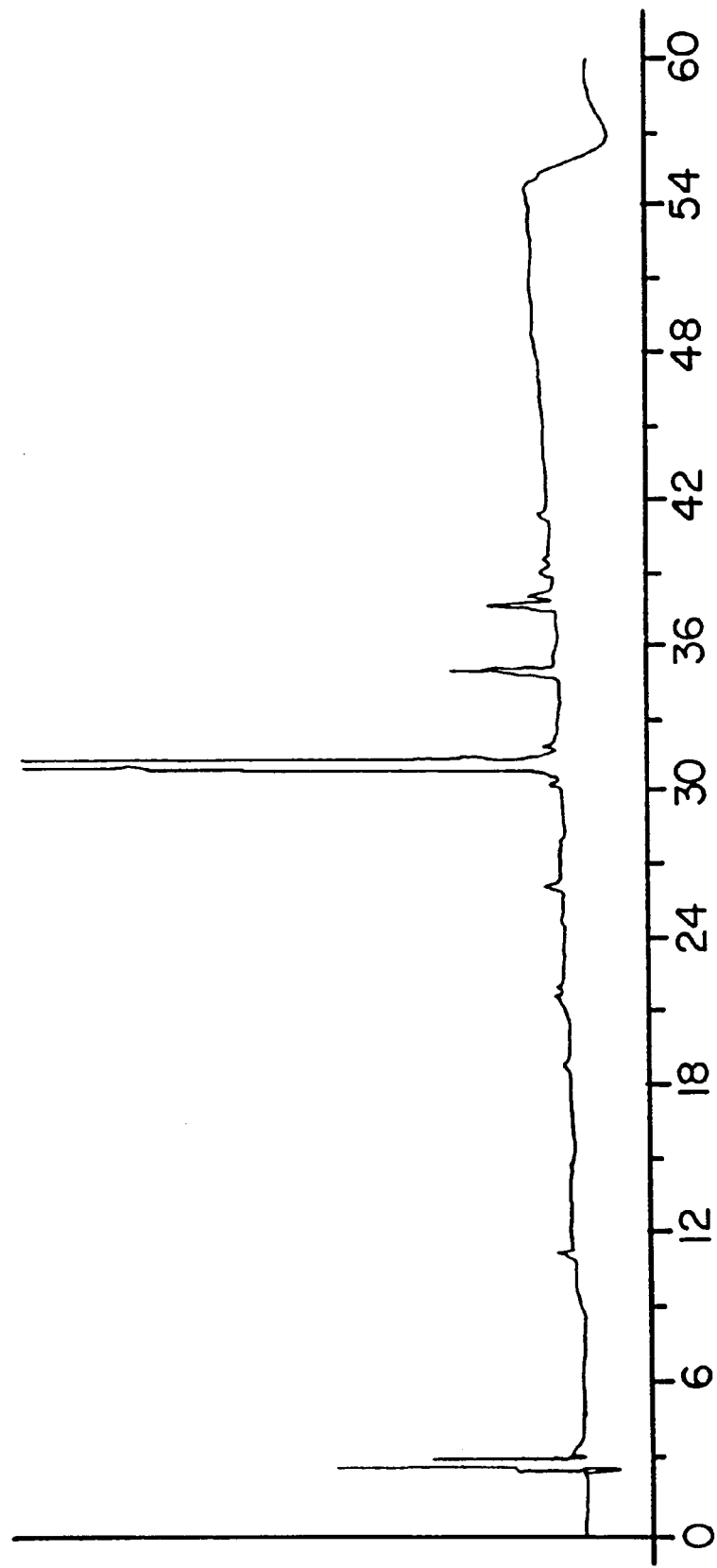
FIG. 2 is a graphic illustration of the high performance chromatography (HPLC) trace of L-Phe-(diketo-L-Asp)-L-Phe.
Figure 3A:
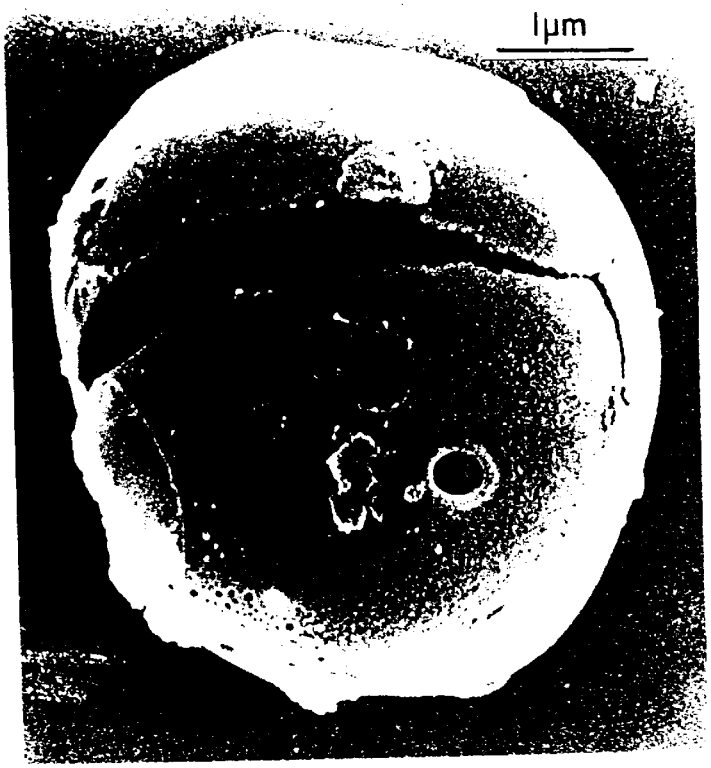
FIGS. 3A and 3B are scanning electron micrographs of L-Phe-(diketo-L-Asp)-L-Phe.
Figure 3B:
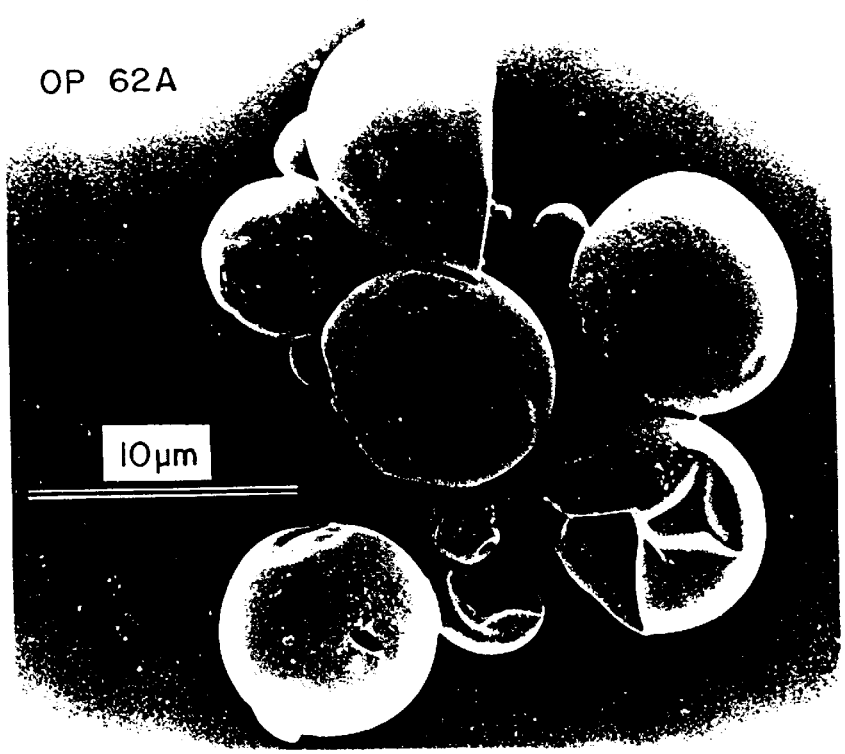

The sample was analyzed using HPLC, the retention time for L-Phe-(diketo-L-Asp)-L-Phe was 31 minutes. Results are illustrated in FIG. 2. The conditions were as follows:

Column: Vydac protein and Peptide, C18, 5 μM particle size, 300 Å pore size; 4.6×250 mm Cat. No. 218TP54.

Mobile Phase A: 0.1% Trifluoro-acetic acid in H$_2$O

Mobile Phase B: 50% CH$_3$CN/50% H$_2$O W/0.1% Trifluoro-acetic acid

Pump: Hitachi L-6200A Intelligent Pump

Flow Rate: 1.0 ml/min.

Detector: UV 220 nm

Linear Gradient:

| STEP | TIME (min) | % A | % B |
| --- | --- | --- | --- |
| 1 | 0 | 100 | 0 |
| 2 | 45 | 0 | 100 |
| 3 | 50 | 0 | 100 |
| 4 | 60 | 100 | 0 |

Steps 1 to 2 define a linear gradient from 100% A to 100% B, step 3 defines a 5 minute hold at 100% B, and step 4 defines a 10 minute re-equilibration at 100% A.

EXAMPLE 19

D-Phe-(diketo-L-Asp)-D-Phe

According to the method of Example 16, D-Phe-(diketo-L-Asp)-D-Phe was prepared by hydrogenation of the dibenzyl ester, Bn-D-Phe-(diketo-L-Asp)-D-Phe-Bn (5.5 g, 7.8 mmol) prepared according to the method of Example 10. The reaction was monitored by TLC (10% EtOH/CHCl$_3$). The resultant crude solid was purified by column chromatography (Sephadex LH-20, 15% EtOH/toluene) to yield D-Phe-(diketo-L-Asp)-D-Phe as a white solid (4.0 g, 98%).

Properties of the amino acids/diketopiperazine carrier are listed below.

m.p. 195–197° C.; $^1$H NMR (CD$_3$OD): δ 7.25 (m, 10H), 4.65 (dt, 2H), 4.21 (t, 2H), 3.21 (dd, 2H), 2.96 (dd, 2H). 2.75 (m, 4H). $^{13}$C NMR (DMSO-d$_6$); δ 172.9, 169.7, 167.1, 137.4, 129.1, 128.2, 126.4, 53.6, 51.2, 37.2, 36.7. Analysis: Calc. for C$_{26}$H$_{28}$N$_4$O$_8$: C 59.54; H 5.38; N 10.68: Found: C 59.45; H 5.43; N 10.58. High resolution mass spectrum; Theoretical: 525.1985 (M+H); Found: 525.1972 (M+H). Optical rotation: [α]$_D$–48° (c=1, DMSO).

EXAMPLE 20

D,L-Phe-(diketo-L-AsD)-D,L-Phe

According to the method of Example 16, D, L-Phe-(diketo-L-Asp)-D, L-Phe was prepared by hydrogenation of the dibenzyl ester Bn-D, L-Phe-(diketo-L-Asp)-D, L-Phe-Bn (0.23 g, 0.33 mmol) prepared according to the method of EXAMPLE 11. The reaction was monitored by TLC (10% EtOH/CHCl$_3$). After all the starting material had been consumed, the catalyst was filtered off, and the filtrate concentrated to yield D,L-Phe-(diketo-L-Asp)-D,L-Phe as a white solid (0.16 g, 94%).

Properties of the amino acids/diketopiperazine carrier are listed below.

m.p. 138–140° C.; $^1$H NMR (d$_6$-DMSO): δ 8.32 (s, 2H), 7.64 (s, 2H), 7.25 (m, 10H), 4.41 (m, 2H), 4.10 (m, 2H), 2.98 (m, 4H), 2.58 (m, 4H). $^3$C NMR (DMSO-d$_6$): δ 173.0, 169.6, 167.1, 137.5, 129.2, 128.2, 126.5, 53.7, 51.1, 38.6, 37.4, 36.8. Analysis: Calc. for C$_{26}$H$_{28}$N$_4$O$_8$: C 59.54; H 5.38, N 10.68: Found: C 59.40; H 5.40; N 10.62. Optical rotation: [α]$_D$–40° (c=1, DMSO).

EXAMPLE 21

L-Phe-(diketo-L-Glu)-L-Phe

According to the procedure of Example 16, L-Phe-(diketo-L-Glu)-L-Phe was prepared by hydrogenation of the dibenzyl ester Bn-L-Phe-(diketo-L-Glu)-L-Phe-Bn (1.00 g, 1.36 mmol) except substituting EtOH (degassed) for the MeOH (degassed). The reaction was monitored by TLC (10% EtOH/CHCl$_3$). The crude solid (0.75 g) was recrystallized in 30% EtOH/EtOAc to provide L-Phe-(diketo-L-Glu)-L-Phe as a white solid (0.31 g, 41%).

Properties of the amino acids/diketopiperazine carrier are listed below.

m.p. 135° C. (sublimes); $^1$H NMR (10% CD$_3$OD/DMSO-d$_6$): δ 7.20 (m, 10H), 4.40 (dd, 2H), 3.68 (t, 2H), 3.05 (dd, 2H), 2.80 (dd, 2H), 2.17 (m, 4H), 1.79 (m, 4H). High resolution mass spectrum (C$_{28}$H$_2$N$_4$O$_8$): Theoretical: 553.2298 (M+H); Found: 553.2219 (M+H). Optical rotation: [α]$_D$–350 (c=0.51, DMSO).

EXAMPLE 22

L-Phe-L-Phe-(diketo-L-Asp)-L-Phe-L-Phe

According to the method of Example 15, L-Phe-L-Phe-(diketo-L-Asp)-L-Phe-L-Phe was prepared by hydrogenation of the dibenzyl ester Bn-L-Phe-L-Phe-(diketo-L-Asp)-L-Phe-L-Phe-Bn (0.92 g, 0.92 mmol) prepared according to the procedure of Example 13 substituting THF as the solvent. The crude solid (0.9 g) was precipitated from boiling EtOAc to yield L-Phe-L-Phe(diketo-L-Asp)-L-Phe-L-Phe (0.61 g. 81%).

Properties of the amino acids/diketopiperazine carrier are listed below.

m.p. 243–247° C.; $^1$H NMR (d$_6$-DMSO): δ 8.25 (t, 4H), 7.20 (m, 20H), 4.47 (m, 2H), 4.37 (q, 2H), 4.15 (t, 2H), 3.00 (m, 6H), 2.67 (m, 4H), 2.31 (dd, 2H). Analysis Calc. for C$_{44}$H$_{46}$N$_6$O$_{10}$: C 64.54; H 5.66; N 10.26: Found: C 64.31; H 5.75; N 10.20. Optical rotation: [α]$_D$–41° (c=1, DMSO).

EXAMPLES 23 and 24

The bis acids of the amino acids/diketopiperazines prepared according to the methods of Examples 18 and 19 (0.1 mmol) were dissolved in 0.1 ml of aqueous Li$_2$CO$_3$ (1M) deionized water to provide a clear solution of the lithium salt. 50 μl of this 1M solution were mixed with 50 μl of 0.86M citric acid. The mixture was shaken to yield a white suspension. Microspheric examination of the suspension revealed the presence of tiny spheres which moved randomly throughout the field of inspection. Spheres ranging in size up to about 10 μ were observed.

EXAMPLE 25

Preparation of Amino Acids/Diketopiperazine/
Salmon Carrier Calcitonin Compositions
Preparation of Diketopiperazine Microspheres Containing
Encapsulated Salmon Calcitonin L-Phe-(diketo-L-Asp)-L-Phe (37 mg) prepared according to the method of Example 18, was dissolved at 40° C. in distilled water (640 μL) with 100 ml of Tris base tris (hydroxymethylamine) in distilled water, to prepare a solution having a carrier concentration of 50 mg/ml. Water was added to bring the total volume to 4.0 ml. The sample had a carrier concentration of 200 mg/mL. Salmon calcitonin (6 μg) and 2M citric acid were added to the solution. The total salmon calcitonin concentration was 1.5 μg/mL. Microspheres containing salmon calcitonin were observed.

EXAMPLE 26

In Vivo Evaluation of Calcitonin Preparations in Rats

Six fasted rats were anesthetized. The rats were administered, by oral gavage, a calcitonin/L-Phe-(diketo-L-Asp)-L-Phe composition containing 1.5 μg of calcitonin/ml was prepared according to the method of Example 25. Each rat was administered a dosage of 10 μg/kg. The amount of diketopiperazine in the dosage was 300 mg/kg.

Figure 4:
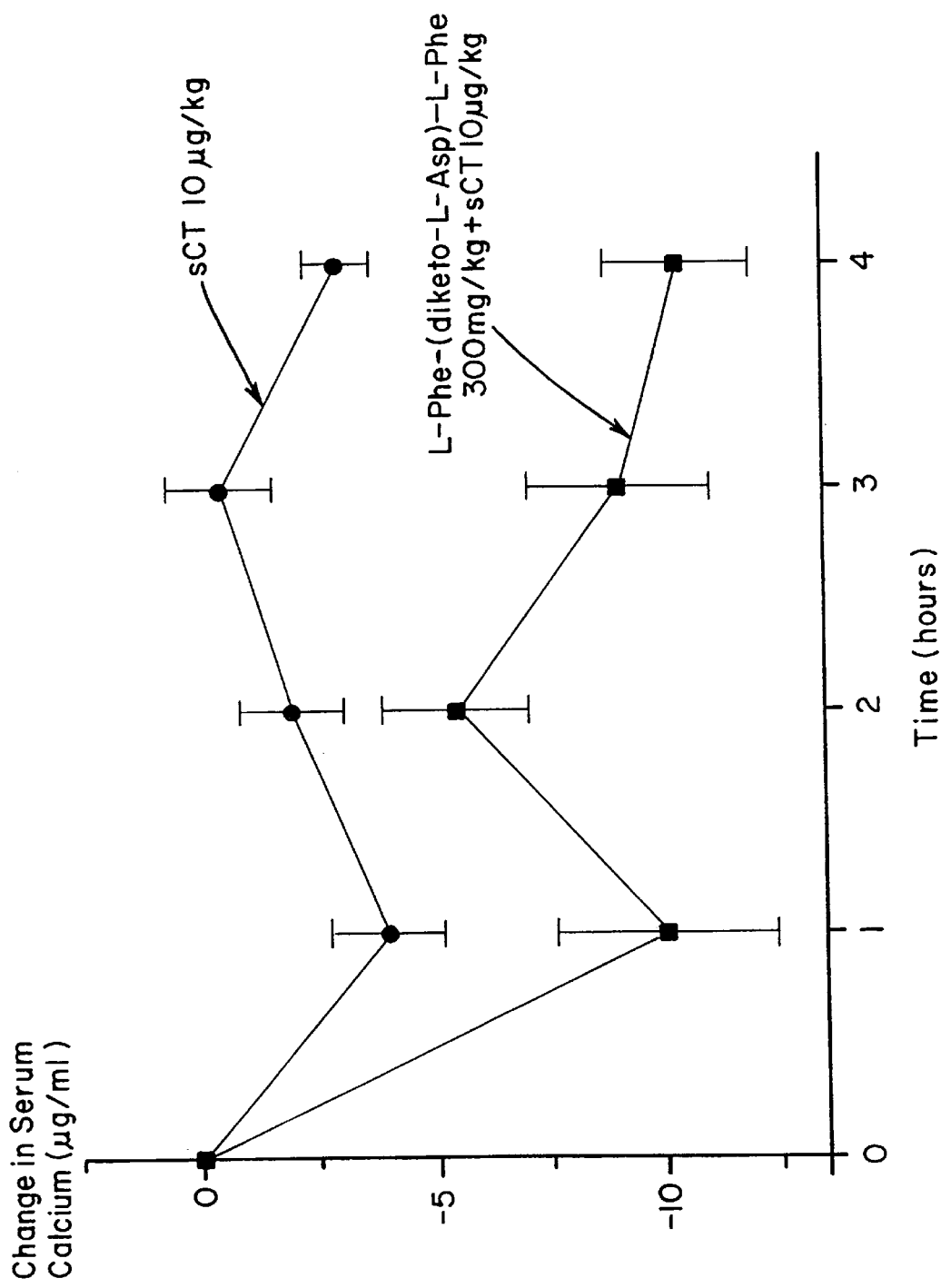
FIG. 4 is a graphic illustration of the results of oral gavage testing in rats using salmon calcitonin with L-Phe-(diketo-L-Asp)-L-Phe carrier.

Blood samples were collected serially from the tail artery. Serum calcium was determined by testing with a Demand™ Calcium Kit (Sigma Chemical Company—St. Louis, Mo.). Results are illustrated in FIG. 4.

Comparative Example 26A

In Vivo Evaluation of Calcitonin Preparations in Rats

A second group of rats was administered, by oral gavage, 10 μg/kg of salmon calcitonin, without any carrier. Results are illustrated in FIG. 4.

Example 26 and Comparative Example 26A illustrate that the carriers of the present invention facilitated the reduction of serum calcitonin and, therefore, the oral delivery of calcitonin.

EXAMPLE 27

In Vivo Evaluation of Interferon Preparations in Rats

A dosing preparation was prepared containing interferon α2b and a carrier of Sarcosine anhydride (the diketopiperazine of N-methyl glycine; formed from sarcosine) (Sigma—St Louis, Mo.) in a Trizma® hydrochloride buffer solution (Tris-HCl) at a pH of about 7–8.

The samples containing the interferon α2b and carrier were administered by oral gavage, to five rats. The dose was 1000 μg/kg. The amount of carrier was 800 mg/kg. Delivery was evaluated by using an ELISA assay (BioScience Int.'l.—Camarillo, Calif.) for human interferon α.

Figure 5:
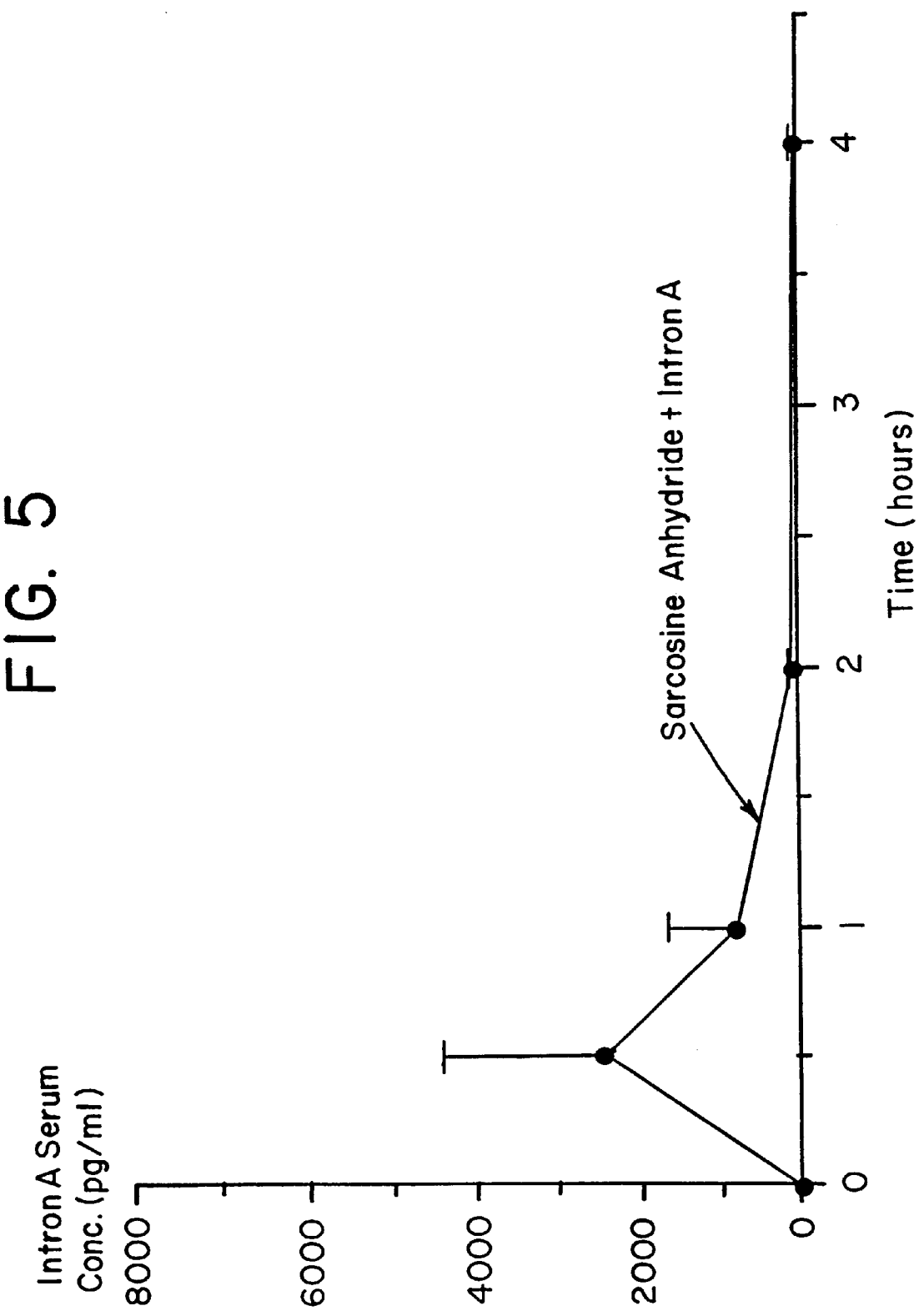
FIG. 5 is a graphic illustration of the results of oral gavage testing in rats using interferon α2b with Sarcosine anhydride carrier.

Results are illustrated in FIG. 5.

EXAMPLE 28

Toxicity Study of L-Phe-(diketo-L-Asp)-L-Phe in Mice

Male mice (BALB/c) were fed a dose of 1 g/kg of L-Phe-(diketo-L-Asp)-L-Phe per day for five (5) days. The compound showed neither acute nor chronic toxicity (over the 5 day period), and no unusual behavior was observed.

EXAMPLE 29

In vitro Enzyme Kinetics of Pancreatin Digestion of Salmon Calcitonin

The following solutions were prepared:

Salmon calcitonin (sCt), 10 mg/ml in 0.085 N citric acid; potassium phosphate (monobasic), 7 mg/ml (titrated to pH 7 with 1 N NaOH); pancreatin, 20 mg/ml in potassium phosphate solution; amino acids/diketopiperazine carrier L-Phe-(diketo-L-Asp)-L-Phe (prepared by dissolving the carrier in potassium phosphate solution, titrating to pH 7.2±0.1 (1 N NaOH or HCl as needed), heating to 37° C., stirring, and filtering through 0.2μ syringe filter.

Eight 1.7 ml eppendorf tubes were prepared. Two ml of the carrier solution were placed in several 5 ml stoppered tubes. Two ml of potassium phosphate solution were placed in control tubes (5 ml). 100 μl of sCT stock solution were added to each 5 ml tube. The solutions were vortexed, and a 100 μl aliquot of each tube was transferred to the first eppendorf tube in each set (baseline). The eppendorf tubes were immediately cooled to −78° C. in a dry ice/acetone bath and stored for analysis at a later time. 100 μl of pancreatin stock solution were added to each tube. The tubes were vortexed. 100 μl of the solution were transferred to a second eppendorf tube and were frozen. The 5 ml tubes with the reagents were placed in a 37° C. water bath for one hour. Samples were obtained at the following times 0 min. (baseline), 0.1 min., 1 min., 5 min., 10 min., min., 30 min., and 60 min. Samples were kept at −70° C. until ready for assay.

Results are illustrated in FIG. 6.

The samples were assayed using HPLC to determine the amount of calcitonin remaining. The conditions were as follows:

Column: RANIN C4 3 cm×4.6 mm, 10 μm particle size, 300 Å pore size (Solvent)

Mobile Phase A: 10% $CH_3CN$/90% $H_2O$ in 20 mM potassium phosphate buffer at pH 7

Mobile Phase B: 60% $CH_3CN$/40% $H_2O$ in 20 mM potassium phosphate buffer at pH 7

Pump: Hitachi L-6200 Intelligent Pump

Linear Gradient:

| STEP | TIME (min) | A | B |
|---|---|---|---|
| 1 | 0 | 70% | 30% |
| 2 | 7 | 40% | 60% |
| 3 | 7.1 | — | 100% |
| 4 | 8.0 | — | 100% |
| 5 | 8.1 | 70% | 30% |

Flow Rate: 2.5 ml/min

Step 1–2 is a linear gradient from 70% A/30% B to 40% A/60% B. Steps 2–3 is a direct charge to 100% B for 0.9 min followed by a direct charge to 70% A/30% B at 8.1 min.

Detector: UV 220 nm

Comparative Example 29A

The procedure of Example 29 was followed omitting the addition of carrier solution to the eppendorf tubes.

Results are illustrated in FIG. 6.

EXAMPLE 30

The procedure of Example 29 was followed substituting D-Phe-(diketo-L-Asp)-D-Phe prepared according to the method of Example 20 for the amino acids/diketopiperazine carrier.

Results are illustrated in FIG. 6.

Examples 29 and 30, when compared with Comparative Example 29A, illustrate that the carriers of the present invention protect the active agent from enzymation degradation.

All patents, applications, test methods, and publications mentioned herein are hereby incorporated by references.

Many variations of the present invention will suggest themselves to those skilled in the art in light of the above detailed disclosure. All such modifications are within the full intended scope of the appended claims.

I claim:

1. A delivery composition comprising:
   (a) an active agent; and
   (b) a diketopiperazine having the formula:

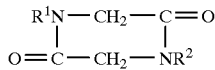

wherein $R^1$, $R^2$, or $R^1$ and $R^2$ independently are hydrogen, $C_1-C_{24}$ alkyl, $C_1-C_{24}$ alkenyl, phenyl, naphtyl, ($C_1-C_{10}$ alkyl)phenyl, ($C_1-C_{10}$ alkenyl) phenyl, ($C_1-C_{10}$ alkyl)naphthyl, ($C_1-C_{10}$ alkenyl) naphthyl, phenyl ($C_1-C_{10}$ alkyl), phenyl ($C_1-C_{10}$ alkenyl), naphthyl ($C_1-C_{10}$ alkyl), and naphthyl ($C_1-C_{10}$ alkenyl);

$R^1$ or $R^2$, or both $R^1$ and $R^2$, optionally, are independently substituted with $C_1-C_4$ alkyl, $C_1-C_4$ alkenyl, $C_1-C_4$ alkoxy, —OH, —SH, and —$CO_2R^3$ or any combination thereof; wherein $R^3$ is hydrogen, $C_1-C_4$ alkyl, or $C_1-C_4$ alkenyl;

$R^1$, $R^2$, or $R^1$ and $R^2$, optionally, are independently interrupted by oxygen, nitrogen, sulfur, or any combination thereof;

said phenyl, naphthyl, or phenyl and naphthyl groups, optionally, are independently substituted by $C_1-C_6$ alkyl, $C_1-C_6$ alkenyl, $C_1-C_6$ alkoxy, —OH, —SH, or $CO_2R^4$ wherein $R^4$ is hydrogen, $C_1-C_6$ alkyl; or $C_1-C_6$ alkenyl; and $R^1$ and $R^2$ are not both hydrogen.

2. A delivery composition as defined in claim 1, comprising a microsphere.

3. A delivery composition as defined in claim 2, wherein said microsphere comprises a microcapsule.

4. A delivery composition as defined in claim 2, wherein said microsphere has a diameter of less than about 10 μm.

5. A delivery composition as defined in claim 1, wherein said active agent comprises a fragrance.

6. A delivery composition as defined in claim 1, wherein said active agent comprises a biologically active agent.

7. A delivery composition as defined in claim 6, wherein said biologically active agent is selected from the group consisting of a peptide, a mucopolysaccharide, a carbohydrate, a lipid, a pesticide, or any combination thereof.

8. The delivery composition as defined in claim 7, wherein said biologically-active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), or any combination of any of the foregoing.

9. A delivery composition as defined in claim 8, wherein said biologically-active agent is selected from the group consisting of an interferon, interleukin-II, insulin, heparin, calcitonin, oxytocin, vasopressin, cromolyn sodium, vancomycin, DFO, or any combination of any of the foregoing.

10. A delivery composition as defined in claim 1, wherein said diketopiperazine is derived from two α-amino acids.

11. A delivery composition as defined in claim 10, wherein said two, α-amino acids from which said diketopiperazine is derived are independently selected from the group consisting of glutamic acid, aspartic acid, tyrosine, phenylalanine, and optical isomers thereof.

12. A delivery composition as defined in claim 10, wherein said two α-amino acids from which said diketopiperazine is derived are the same.

13. A delivery composition as defined in claim 10, wherein said diketopiperazine is prepared by the thermal condensation of said two α-amino acids from which said diketopiperazine is derived.

14. A pharmacological composition comprising:
    (a) at least one pharmacologically active agent; and
    (b) a diketopiperazine having the formula:

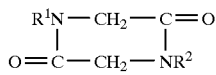

wherein $R^1$, $R^2$, or $R^1$ and $R^2$ independently are hydrogen, $C_1-C_{24}$ alkyl, $C_1-C_{24}$ alkenyl, phenyl, naphthyl, ($C_1-C_{10}$ alkyl)phenyl, ($C_1-C_{10}$ alkenyl) phenyl, ($C_1-C_{10}$ alkyl)naphthyl, ($C_1-C_{10}$ alkenyl) naphthyl, phenyl ($C_1-C_{10}$ alkyl), phenyl ($C_1-C_{10}$ alkenyl), naphthyl ($C_1-C_{10}$ alkyl), and naphthyl ($C_1-C_{10}$ alkenyl);

$R^1$ or $R^2$, or both $R^1$ and $R^2$, optionally, are independently substituted with $C_1-C_4$ alkyl, $C_1-C_4$ alkenyl, $C_1-C_4$ alkoxy, —OH, —SH, and —$CO_2R^3$ or any combination thereof; wherein $R^3$ is hydrogen, $C_1-C_4$ alkyl, or $C_1-C_4$ alkeny;

$R^1$, $R^2$, or $R^1$ and $R^2$, optionally, are independently interrupted by oxygen, nitrogen, sulfur, or any combination thereof;

said phenyl, naphthyl, or phenyl and naghthyl groups, optionally, are independently substituted by $C_1-C_6$ alkyl, $C_1C_6$ alkenyl, $C_1-C_6$ alkoxy, —OH, —SH, or $CO_2R^4$ wherein $R^4$ is hydrogen, $C_1-C_6$ alkyl, or $C_1-C_6$ alkenyl; and $R^1$ and $R^2$ are not both hydrogen.

15. A dosage unit form comprising:
    (A) a delivery composition as defined in claim 1; and
    (B) (a) an excipient, (b) a diluent,
(c) a disintegrant,
(d) a lubricant,
(e) a plasticizer,
(f) a colorant,
(g) a dosing vehicle, or
(h) any combination thereof.

16. A dosage unit form as defined in claim 14, comprising an oral dosage unit form.

17. A dosage unit form as defined in claim 15, selected from the group consisting of a tablet, a capsule, and a liquid.

18. A method for administering a biologically active agent to an animal in need of such agent, said method comprising administering orally to said animal, a composition as defined in claim 11.

19. A method for preparing a delivery composition, said method comprising:
(A) mixing
   (a) an active agent; and
   (b) a diketopiperazine having the formula:

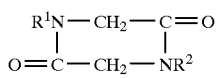

wherein $R^1$, $R^2$, or $R^1$ and $R^2$ independently are hydrogen, $C_1$–$C_{24}$ alkyl, $C_1$–$C_{24}$ alkenyl, phenyl, naphthyl, ($C_1$–$C_{10}$ alkyl)phenyl, ($C_1$–$C_{10}$ alkenyl)phenyl, ($C_1$–$C_{10}$ alkyl)naphthyl, ($C_1$–$C_{10}$ alkenyl)naphthyl, phenyl ($C_1$–$C_{10}$ alkyl), phenyl ($C_1$–$C_{10}$ alkeny), naphthyl ($C_1$–$C_{10}$ alkyl), and naphthyl ($C_1$–$C_{10}$ alkenyl);

$R^1$ or $R^2$, or both $R^1$ and $R^2$, optionally, are independently substituted with $C_1$–$C_4$ alkyl, $C_1$–$C_4$ alkenyl, $C_1$–$C_4$ alkoxy, —OH, —SH, and —$CO_2R^3$ or any combination thereof; wherein $R^3$ is hydrogen, $C_{1-C4}$ alkyl, or $C_1$–$C_4$ alkenyl;

$R^1$, $R^2$, or $R^1$ and $R^2$, optionally, are independently interrupted by oxygen, nitrogen, sulfur, or any combination thereof;

said phenyl, naphthyl, or phenyl and naphthyl groups, optionally, are independently substituted by $C_1$–$C_6$ alkyl, $C_1$–$C_6$ alkenyl, $C_1$–$C_6$ alkoxy, —OH, —SH, or $CO_2R^4$ wherein $R^4$ is hydrogen, $C_1$–$C_6$ alkyl, or $C_1$–$C_6$ alkenyl; and $R^1$ and $R^2$ are not both hydrogen.

20. A method for preparing microspheres containing an active agent, said method comprising:
(A) solubilizing, in a solvent, a diketopiperazine having the formula:

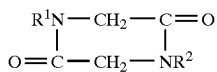

wherein $R^1$, $R^2$, or $R^1$ and $R^2$ independently are hydrogen, $C_1$–$C_{24}$ alkyl, $C_1$–$C_{24}$ alkenyl, phenyl, naphthyl, ($C_1$–$C_{10}$ alkyl)phenyl, ($C_1$–$C_{10}$ alkenyl)phenyl, ($C_1$–$C_{10}$ alkyl)naphthyl, ($C_1$–$C_{10}$ alkenyl)naphthyl, phenyl ($C_1$–$C_{10}$ alkyl), phenyl ($C_1$–$C_{10}$ alkeny), naphthyl ($C_1$–$C_{10}$ alkyl), and naphthyl ($C_1$–$C_{10}$ alkenyl);

$R^1$ or $R^2$, or both $R^1$ and $R^2$, optionally, are independently substituted with $C_1$–$C_4$ alkyl, $C_1$–$C_4$ alkenyl, $C_1$–$C_4$ alkoxy, —OH, —SH, and —$CO_2R^3$ or any combination thereof; $R^3$ is hydrogen, $C_1$–$C_4$ alkyl or $C_1$–$C_4$ alkenyl;

$R^1$, $R^2$, or $R^1$ and $R^2$, optionally, are independently interrupted by oxygen, nitrogen, sulfur, or any combination thereof;

said phenyl, naphthyl, or phenyl and naphthyl groups, optionally, are independently substituted by $C_1$–$C_6$ alkyl, $C_1$–$C_6$ alkenyl, $C_1$–$C_6$ alkoxy, —OH, —SH, or $CO_2R^4$ wherein $R^4$ is hydrogen, $C_1$–$C_6$ alkyl, or $C_1$–$C_6$ alkenyl; and $R^1$ and $R^2$ are not both hydrogen, to yield a diketopiperazine solution; and (B) contacting said diketopiperazine solution with said active agent and a precipitator solution in which said diketopiperazine is insoluble.

21. A method as defined in claim 20, wherein said diketopiperazine solution has a pH within a first range and said precipitator solution has a pH within a second range, said first range being different than said second range.

22. A delivery composition comprising:
(a) an active agent; and
(b) a diketopiperazine having the formula

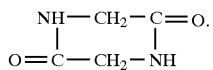

23. A delivery composition as defined in claim 22, comprising a microsphere.

24. A delivery composition as defined in claim 23, wherein said microsphere comprises a microcapsule.

25. A delivery composition as defined in claim 23, wherein said microsphere has a diameter of less than about 10 µm.

26. A delivery composition as defined in claim 22, wherein said active agent comprises a fragrance.

27. A delivery composition as defined in claim 22, wherein said active agent comprises a biologically active agent.

28. A delivery composition as defined in claim 27, wherein said biologically active agent is selected from the group consisting of a peptide, a mucopolysaccharide, a carbohydrate, a lipid, a pesticide, or any combination of any of the foregoing.

29. A delivery composition as defined in claim 27, wherein said biologically-active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), or any combination of any of the foregoing.

30. A delivery composition as defined in claim 29, wherein said biologically-active agent is selected from the group consisting of an interferon, interleukin-II, insulin, heparin, calcitonin, oxytocin, vasopressin, cromolyn sodium, vancomycin, DFO, or any combination of any of the foregoing.

31. A pharmacological composition comprising:
(A) at least one pharmacologically active agent; and
(B) a carrier comprising a diketopiperazine having the formula:

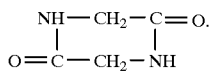

32. A dosage unit form comprising:
(A) a delivery composition as defined in claim 22; and
(B) (a) an excipient,
   (b) a diluent,
   (c) a disintegrant,
   (d) a lubricant,
   (e) a plasticizer,
   (f) a colorant,
   (g) a dosing vehicle, or
   (h) any combination thereof.

33. A dosage unit form as defined in claim 32, comprising an oral dosage unit form.

34. A dosage unit form as defined in claim 32, selected from the group consisting of a tablet, a capsule, and a liquid.

35. A method for administering a biologically active agent to an animal in need of such agent, said method comprising administering orally to said animal, a delivery composition as defined in claim 22.

36. A method for preparing a delivery composition, said method comprising:
(A) mixing
   (a) an active agent; and
   (b) a carrier comprising a diketopiperazine having the formula

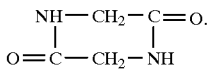

37. A method for preparing microspheres containing an active agent, said method comprising
(A) solubilizing, in solvent, a carrier comprising a diketopiperazine having the formula

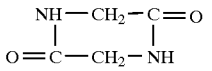

and;
(B) contacting said carrier solution with said active agent and a precipitator solution in which said carrier is insoluble.

38. A method as defined in claim 37, wherein said carrier solution has a pH within a first range and said precipitator solution has a pH within a second range, said first range being different than said second range.

* * * * *